US009901546B2

(12) United States Patent
Shimizu et al.

(10) Patent No.: US 9,901,546 B2
(45) Date of Patent: *Feb. 27, 2018

(54) ORALLY DISINTEGRABLE TABLETS

(71) Applicant: Takeda Pharmaceutical Company Limited, Osaka (JP)

(72) Inventors: Toshihiro Shimizu, Itami (JP); Shuji Morimoto, Suita (JP); Tetsuro Tabata, Suita (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/287,740

(22) Filed: May 27, 2014

(65) Prior Publication Data

US 2014/0271856 A1 Sep. 18, 2014

Related U.S. Application Data

(63) Continuation of application No. 12/967,858, filed on Dec. 14, 2010, now abandoned, which is a continuation of application No. 12/151,572, filed on May 7, 2008, now Pat. No. 7,875,292, which is a continuation of application No. 10/017,755, filed on Oct. 30, 2001, now Pat. No. 7,431,942, which is a continuation of application No. 09/355,781, filed as application No. PCT/JP99/02548 on May 17, 1999, now Pat. No. 6,328,994.

(30) Foreign Application Priority Data

| May 18, 1998 | (JP) | 10-135472 |
| Aug. 3, 1998 | (JP) | 10-219266 |
| Aug. 5, 1998 | (JP) | 10-222151 |
| Jan. 12, 1999 | (JP) | 11-005144 |
| Jan. 25, 1999 | (JP) | 11-015851 |

(51) Int. Cl.
| *A61K 9/26* | (2006.01) |
| *A61K 9/28* | (2006.01) |
| *A61K 9/00* | (2006.01) |
| *A61K 9/16* | (2006.01) |
| *A61K 9/20* | (2006.01) |
| *A61K 9/50* | (2006.01) |
| *A61K 31/4439* | (2006.01) |

(52) U.S. Cl.
CPC ............. *A61K 9/28* (2013.01); *A61K 9/0056* (2013.01); *A61K 9/1611* (2013.01); *A61K 9/1652* (2013.01); *A61K 9/2081* (2013.01); *A61K 9/5026* (2013.01); *A61K 9/5042* (2013.01); *A61K 9/5073* (2013.01); *A61K 31/4439* (2013.01)

(58) Field of Classification Search
None
See application file for complete search history.

(56) References Cited

U.S. PATENT DOCUMENTS

| 4,371,516 A | 2/1983 | Wyeth |
| 4,710,384 A | 12/1987 | Rotman |
| 4,749,575 A | 6/1988 | Avner |
| 4,753,804 A | 6/1988 | Iaccheri et al. |
| 4,830,853 A | 5/1989 | Murthy et al. |
| 4,871,549 A | 10/1989 | Ueda et al. |
| 4,936,074 A | 6/1990 | Graham |
| 5,045,321 A | 3/1991 | Makino |
| 5,017,122 A | 5/1991 | Staniforth |
| 5,026,560 A | 6/1991 | Makino et al. |
| 5,178,878 A | 1/1993 | Wehling et al. |
| 5,433,959 A | 7/1995 | Makino |
| 5,441,933 A | 8/1995 | Lattanzi et al. |
| 5,464,632 A | 11/1995 | Cousin et al. |
| 5,501,861 A | 3/1996 | Makino et al. |

(Continued)

FOREIGN PATENT DOCUMENTS

| EP | 0 336 298 | 3/1989 |
| EP | 0 345 787 | 6/1989 |

(Continued)

OTHER PUBLICATIONS

Watanabe, et al., "New Compressed Tablet Rapidly Disintegrating in Saliva in the Mouth using Crystalline Cellulose and a Disintegrant", Biol. Pharm. Bull., vol. 18, No. 9, pp. 1308-1310, 1995.

Lehman, et al., "Fast Disintegrating Controlled Release Tablets from Coated Particles", Drugs Made in Germany, 37(2), 53-60, 1994.

Shimizu, et al., "Formulation Study for Lansoprazole Fast-disintegrating Tablet. I. Effect of Compression on Dissolution Bahavior", Chem. Pharm. Bull. 51(8), 942-947, 2003.

Notice of Opposition to a European Patent—dated Sep. 21, 2007.

Martin, "Physical Pharmacy—Physical Chemical Principles in the Pharmaceutical Sciences", $4^{th}$ Edition, Lea and Febiger, 1993, pp. 557-560.

(Continued)

*Primary Examiner* — Susan Tran
(74) *Attorney, Agent, or Firm* — Hamre, Schumann, Mueller & Larson, P.C.

(57) ABSTRACT

An orally disintegrable tablet, of the present invention, which comprises (i) fine granules having an average particle diameter of 400 μm or less, which fine granules comprise a composition coated by an enteric coating layer, said composition having 10 weight % or more of an acid-labile physiologically active substance and (ii) an additive, has superior disintegrability or dissolution in the oral cavity so that it can be used for treatment or prevention of various diseases, as an orally disintegrable tablet capable of being administered to the aged or children and easily administered without water. Also, because the tablet of the present invention contains fine granules having the average particle diameter such that it will not impart roughness in mouth, it can be administered easily without discomfort at the administration.

22 Claims, No Drawings

(56) References Cited

U.S. PATENT DOCUMENTS

| | | | |
|---|---|---|---|
| 5,549,911 A | | 8/1996 | Ledue et al. |
| 5,576,014 A | | 11/1996 | Mizumoto et al. |
| 5,656,284 A | | 8/1997 | Balkin |
| 5,720,974 A | | 2/1998 | Makino et al. |
| 5,792,473 A | | 8/1998 | Gergely et al. |
| 5,795,909 A | | 8/1998 | Shashoua et al. |
| 5,798,120 A | | 8/1998 | Tomohisa et al. |
| 5,824,339 A | | 10/1998 | Shimizu et al. |
| 5,855,914 A | | 1/1999 | Koyama et al. |
| 5,869,098 A | | 2/1999 | Misra et al. |
| 5,900,428 A | | 5/1999 | Fandriks et al. |
| 5,935,600 A | | 8/1999 | Cherukuri et al. |
| 5,958,453 A | | 9/1999 | Ohno et al. |
| 5,965,162 A | * | 10/1999 | Fuisz .................. A23G 3/0289 424/441 |
| 6,024,981 A | * | 2/2000 | Khankari et al. ............. 424/464 |
| 6,132,770 A | * | 10/2000 | Lundberg ...................... 424/466 |
| 6,248,357 B1 | | 6/2001 | Ohno et al. |
| 6,287,596 B1 | | 9/2001 | Murakami et al. |
| 6,299,904 B1 | | 10/2001 | Shimizu et al. |
| 6,328,994 B1 | | 12/2001 | Shimizu et al. |
| 6,365,184 B1 | | 4/2002 | Depui et al. |
| 6,380,234 B1 | | 4/2002 | Makino et al. |
| 6,471,992 B1 | | 10/2002 | Yoo et al. |
| 6,531,152 B1 | | 3/2003 | Lerner et al. |
| 6,586,004 B2 | | 7/2003 | Shimizu et al. |
| 7,431,942 B2 | | 10/2008 | Shimizu |

FOREIGN PATENT DOCUMENTS

| | | |
|---|---|---|
| EP | 0 365 480 | 10/1989 |
| EP | 0 446 961 | 9/1991 |
| EP | 0 452 862 | 10/1991 |
| EP | 0 553 777 | 1/1993 |
| EP | 0 638 310 | 7/1994 |
| EP | 0 745 382 | 1/1995 |
| EP | 0 438 147 | 1/1997 |
| EP | 0 890 359 | 2/1997 |
| EP | 0 761 212 | 3/1997 |
| EP | 0 914 818 | 6/1997 |
| EP | 0 922 464 | 7/1997 |
| EP | 0 799 616 | 10/1997 |
| EP | 0 839 526 | 10/1997 |
| EP | 0 965 339 | 11/1997 |
| GB | 2 147 501 | 10/1984 |
| JP | 54-11226 | 1/1979 |
| JP | 1-268627 | 10/1989 |
| JP | 1-268628 | 10/1989 |
| JP | 4-066538 | 3/1992 |
| JP | 5-92918 | 4/1993 |
| JP | 5-310558 | 11/1993 |
| JP | 6-100601 | 4/1994 |
| JP | 6-305962 | 11/1994 |
| JP | 7-017853 | 1/1995 |
| JP | 8-27033 | 1/1996 |
| JP | 8-310969 | 11/1996 |
| JP | 9-48726 | 2/1997 |
| JP | 9-71523 | 3/1997 |
| WO | 87/02240 | 4/1987 |
| WO | 92/11001 | 7/1992 |
| WO | 95/10264 | 4/1995 |
| WO | 96/01623 | 1/1996 |
| WO | 96/01624 | 1/1996 |
| WO | 96/24375 | 8/1996 |
| WO | 97/04728 | 2/1997 |
| WO | 97/25065 | 7/1997 |
| WO | 97/25066 | 7/1997 |
| WO | 97/25979 | 7/1997 |
| WO | 97/49394 | 12/1997 |
| WO | 98/53798 | 12/1998 |
| WO | 99/59544 | 11/1999 |
| WO | 00/06126 | 2/2000 |

OTHER PUBLICATIONS

Martin, "Physikalische Pharmazie—Pharmazeutisch angewandte physikalisch-chemische Grundlagen", $4^{th}$, fully revised an extended edition, Wissenschaftiliche Verlagsgessellschaft mbH Stuttgart, 2002, pp. 730-731 with an English Translation.

* cited by examiner

ORALLY DISINTEGRABLE TABLETS

CROSS REFERENCE TO RELATED APPLICATIONS

This application is a Continuation of application Ser. No. 12/967,858, filed Dec. 14,2010 and now abandoned, which is a Continuation of application Ser. No. 12/151,572, filed May 7, 2008, now issued U.S. Pat. No. 7,875,292, which is a Continuation of Ser. No. 10/017,755, filed Oct. 30, 2001, now issued U.S. Pat. No. 7,431,942, which is a Continuation of application Ser. No. 09/355,781, filed Aug. 4, 1999, now issued U.S. Pat. No. 6,328,994, which is a U.S. National Stage of Application No. PCT/JP99/02548, filed May 17, 1999, which is incorporated herein by reference.

TECHNICAL FIELD

The present invention relates to an orally disintegrable tablet having a characteristic of fast disintegration in the oral cavity even without water.

BACKGROUND ART

Pharmaceutical solid preparations, for example, tablets, usually are prepared to make pharmaceutically active ingredients absorb in a digestive organ by disintegration or dissolution through oral administration, without fast disintegration or dissolution in the oral cavity.

JP-A-6-502194 (U.S. Pat. No. 5,464,632) discloses a rapidly disintegrable multiparticulate tablet, the excipient mixture of which is suitable for imparting a disintegration rate such that the tablet disintegrates in the mouth in less than sixty seconds, characterized by the fact that the active substance is present in the form of coated microcrystals or coated or uncoated microgranules. However, there is no disclosure of an acid-labile physiologically active substance with a basic inorganic salt as the active substance, weight percentage of the active substance in the excipient mixture, or the size of the coated microgranule.

On the other hand, JP-A-5-92918 discloses a powder consisting of a fine-particle core coated with a water-soluble high molecular compound and at least one physiologically active substance, and having a granule size of practically up to 500 μm. However, there is no disclosure of an acid-labile physiologically active substance with a basic inorganic salt as the physiologically active substance, weight percentage of the active substance in the coated granule or the size of the coated granule.

JP-A-63-301816 and U.S. Pat. No. 5,026,560 disclose spherical granules having a core coated with spraying powder containing a drug and low substituted hydroxypropylcellulose. However, there is no disclosure of orally disintegrable tablet.

EP-A-0452862 discloses a spherical granule obtained by coating a pharmacologically inactive spherical seed core having at least 50 weight % microcrystalline cellulose and an average particle size of 100-1000 μm, with a powder comprising an active ingredient, by using an aqueous binding solution, and spraying an aqueous solution or suspension of a coating agent thereon. However, most of the particle sizes of thus obtained granules are 500 μm or more.

JP-A-1-268627, JP-A-1-268628 and JP-A-8-27033 disclose pharmaceutical compositions using erythritol, respectively. However, there is no disclosure of solid pharmaceutical composition characterized fast disintegration in the oral cavity.

JP-A-9-48726 discloses a buccal formulation consisting of a drug and a substance wetting in a mouldable way on humidifying, and retaining a shape after moulding and drying. As such substance, sugars, sugar alcohols and water-soluble polymers are exemplified.

JP-A-5-271054 discloses production of fast dissolving tablets comprising an active ingredient and sugars.

JP-A-9-71523 discloses a tablet with rapid disintegration in the oral cavity comprising medicine, crystalline cellulose, low-substituted hydroxypropyl cellulose and lubricant.

However, these prior art references nowhere disclose an acid-labile physiologically active substance with a basic inorganic salt as an active substance, weight percentage of the active substance in the tablet or the size of the coated fine granule.

To accompany an aging population and their changes in life environment, it is desired to develop an orally disintegrable solid preparation capable of being administered without water, retaining the convenience for use which is a characteristic of a tablet, and being administered on demand easily, anytime and anywhere, without water.

Conventional granules have large particle diameters, which results in inferior workability when dispensing, and also results in difficulties in consistently adding a regular amount of the granules when they are combined into tablets or capsules. Granules having a large particle diameter (400 μm or more of average particle diameter) also produce a feeling of roughness in the mouth. Accordingly, especially when used in an orally disintegrable tablet, the average particle diameter of the included granules must be about 400 μm or less, preferably about 350 μm.

For many reasons, such as, masking a bitter taste, or providing enteric abilities or release abilities, it is desirable to prepare the solid pharmaceutical preparations as granules (or fine granules). In particular, in case of granules or fine granules in which the active ingredient of the drug is enteric coated to impart enteric dissolution, there is a need for enteric coating to prevent dissolution by stomach acid (i.e., to make the preparation acid-resistance). It is necessary to coat the whole surface of the particle—before the enteric coating—(including a case of the crystal of physiologically active substance only, and a case of the granule produced by granulation), with the enteric coating. Namely, at least some uniform thickness (at least 20 μm or more) of the coating layer is needed. Even a portion of thin and weak coating, is undesirable because acid-resistance is lowered. Accordingly, before the enteric coating, it is necessary that the particle is as spherical with smooth surface as possible in form, as uniform as possible in size, and has less cavity.

It is very difficult to produce an enteric coated fine granule with an average particle diameter of 400 μm or less, when the coating is performed so that at least 20 μm thickness of coating layer may coat the whole particle, and the enteric coated particle contains a basic inorganic salt for stabilization of an acid-labile physiologically active substance, and where it contains binders for maintaining the strength of the particle and/or disintegrants for maintaining the disintegrability (dissolution) of the particles. Further, in the case where the content of the acid-labile physiologically active substance is increased, it is necessary to also increase the content of the excipients such as basic inorganic salt, binders and disintegrants. Furthermore, it is very difficult to produce a small enteric coated fine granule containing the physiologically active substance in high content.

Accordingly, it is desired to develop a fine granule which is coated with the enteric coating layer on the composition containing the physiologically active substance such as a physiologically active substance containing a basic inorganic salt and which has a particle diameter so that roughness or oral discomfort is not felt, to develop a fine granule containing the physiologically active substance, i.e., the active ingredients of drugs, and so forth, in high content, to develop a fine granule keeping enteric dissolution, a disintegrability and dissolution and suitable strength, and to develop an orally disintegrable preparation containing such a fine granule, being a fast disintegration type, showing superior oral disintegrability and dissolution and having suitable strength (hardness) so that it will not be damaged through production processes or handling.

In particular, there is a need to combine an acid-labile physiologically active substance, with basic inorganic salts and so forth for stability, and further to coat with coating layers such as an enteric layer. In such cases, it is an important problem to produce an small enteric coated fine granule, even though it contains the acid-labile physiologically active substance in high concentration and in high content.

DISCLOSURE OF INVENTION

The present invention relates to:

[1] an orally disintegrable tablet which comprises (i) fine granules having an average particle diameter of 400 μm or less, which fine granules comprise a composition coated by an enteric coating layer, said composition having 10 weight % or more of an acid-labile physiologically active substance and (ii) an additive;

[2] an orally disintegrable tablet of the above [1], wherein the average particle diameter of the fine granules is 300 to 400 μm;

[3] an orally disintegrable tablet of the above [1], wherein the fine granules further comprise a basic inorganic salt;

[4] an orally disintegrable tablet of the above [1], wherein the additive comprises a water-soluble sugar alcohol;

[5] an orally disintegrable tablet of the above [1], wherein the composition coated by an enteric coating layer is further coated by a coating layer which comprises a water-soluble sugar alcohol;

[6] an orally disintegrable tablet of the above [4], wherein the additive comprises (i) crystalline cellulose and/or (ii) low-substituted hydroxypropyl cellulose;

[7] an orally disintegrable tablet of the above [1], wherein the particle diameter of the fine granules is practically 425 μm or less;

[8] an orally disintegrable tablet of the above [1], wherein the particle diameter of the fine granules is practically 400 μm or less;

[9] an orally disintegrable tablet of the above [1], wherein the acid-labile physiologically active substance is a benzimidazole compound or a salt thereof;

[10] an orally disintegrable tablet of the above [9], wherein the benzimidazole compound is lansoprazole;

[11] an orally disintegrable tablet of the above [3], wherein the basic inorganic salt is a salt of magnesium and/or a salt of calcium;

[12] an orally disintegrable tablet of the above [1], wherein the composition comprises a core being coated by a benzimidazole compound and a basic inorganic salt, said core comprising crystalline cellulose and lactose;

[13] an orally disintegrable tablet of the above [12], wherein the core comprises 50 weight % or more of lactose;

[14] an orally disintegrable tablet of the above [12], wherein the core comprises 40 to 50 weight % of crystalline cellulose and 50 to 60 weight % of lactose;

[15] an orally disintegrable tablet of the above [1], wherein the composition comprises 20 weight % or more of an acid-labile physiologically active substance;

[16] an orally disintegrable tablet of the above [1], wherein the composition comprises 20 to 50 weight % of an acid-labile physiologically active substance;

[17] an orally disintegrable tablet of the above [1], wherein the fine granules are produced by fluidized-bed granulation method;

[18] an orally disintegrable tablet of the above [1], wherein the enteric coating layer comprises an aqueous enteric polymer agent;

[19] an orally disintegrable tablet of the above [18], wherein the aqueous enteric polymer agent is a methacrylic acid copolymer;

[20] an orally disintegrable tablet of the above [18], wherein the enteric coating layer further comprises a sustained-release agent;

[21] an orally disintegrable tablet of the above [20], wherein the sustained-release agent is a methacrylate copolymer;

[22] an orally disintegrable tablet of the above [20], wherein the sustained-release agent is in an amount of 5 to 15 weight % relative to 100 weight % of the aqueous enteric polymer agent;

[23] an orally disintegrable tablet of the above [4], wherein the water-soluble sugar alcohol is erythritol;

[24] an orally disintegrable tablet of the above [4], wherein the water-soluble sugar alcohol is mannitol;

[25] an orally disintegrable tablet of the above [5], wherein the water-soluble sugar alcohol is in an amount of 5 to 97 weight relative to 100 weight % of the orally disintegrable tablet apart from the fine granules;

[26] an orally disintegrable tablet of the above [4], wherein the crystalline cellulose is in an amount of 3 to 50 weight % relative to 100 weight % of the tablet apart from the fine granule;

[27] an orally disintegrable tablet of the above [6], wherein the content of hydroxypropoxyl group in the low-substituted hydroxypropyl cellulose is 7.0 to 9.9 weight %;

[28] an orally disintegrable tablet of the above [6], wherein the content of hydroxypropoxyl group in the low-substituted hydroxypropyl cellulose is 5.0 to 7.0 weight %;

[29] an orally disintegrable tablet of the above [1], which further comprises crospovidone;

[30] an orally disintegrable tablet of the above [1], wherein the oral disintegration time is one minute or less;

[31] an orally disintegrable tablet of the above [1], which comprises no lubricant inside the tablet;

[32] fine granules having an average particle diameter of 400 μm or less, which comprise a composition coated by an enteric coating layer, said composition having (i) 25 weight % or more of an acid-labile physiologically active substance and (ii) a basic inorganic salt;

[33] fine granules of the above [32], wherein the average particle diameter of the fine granules is 300 to 400 μm;

[34] fine granules of the above [32], wherein the particle diameter of the fine granules is practically 425 μm or less;

[35] fine granules of the above [32], wherein the particle diameter of the fine granules is practically 400 μm or less;

[36] fine granules of the above [32], wherein the acid-labile physiologically active substance is a benzimidazole compound or a salt thereof;

[37] fine granules of the above [36], wherein the benzimidazole compound is lansoprazole;

[38] fine granules of the above [32], wherein the basic inorganic salt is a salt of magnesium and/or a salt of calcium;

[39] fine granules of the above [32], wherein the composition comprises a core being coated by a benzimidazole compound and a basic inorganic salt, said core comprising crystalline cellulose and lactose;

[40] fine granules of the above [39], wherein the core comprises 50 weight % or more of lactose;

[41] fine granules of the above [32], wherein the composition comprises 25 to 40 weight % of an acid-labile physiologically active substance;

[42] fine granules of the above [32], which are produced by fluidized-bed granulation method;

[43] fine granules of the above [32], wherein the enteric coating layer comprises an aqueous enteric polymer agent;

[44] fine granules of the above [43], wherein the aqueous enteric polymer agent is a methacrylate copolymer;

[45] fine granules of the above [43], wherein the enteric coating layer further comprise a sustained-release agent;

[46] fine granules of the above [45], wherein the sustained-release agent is a methacrylate copolymer;

[47] fine granules of the above [45], wherein the sustained-release agent is in an amount of 5 to 15 weight % relative to 100 weight % of the aqueous enteric polymer agent;

[48] fine granules of the above [32], wherein the enteric coating layer is in an amount of 50 to 70 weight relative to 100 weight % of the fine granules;

[49] a tablet, granule, fine granule, capsule, effervescent or suspension preparation which comprises the fine granules of the above [32], and so forth.

In the present specification, "coating" means also partial coating and adhesion or adsorption in addition to coating the whole surface of an Object (e.g., core) which is to be coated.

"Spherical" means also forms having a curved surface such as forms having elliptic cross sections, and forms in the shapes of eggplants and drops in addition to spheres.

"Average particle diameter" means volume based distribution median diameter (median diameter: 50% particle diameter from cumulative distribution), unless otherwise specified. It can be measured by, for example, a laser diffraction particle distribution measurement method. Concretely exemplified is a method using Raser Diffraction Analyzer, type: HEROS RODOS [trade name; manufactured by Sympatec (Germany)].

"An orally disintegrable tablet" of the present invention comprises (i) fine granules having an average particle diameter of 400 µm or less, which fine granules comprise a composition coated by an enteric coating layer, said composition having 10 weight % or more of an acid-labile physiologically active substance and (ii) an additive.

In the present, invention, "fine granules having an average particle diameter of 400 µm or less, which fine granules comprise a composition coated by an enteric coating layer, said composition having 10 weight % or more of an acid-labile physiologically active substance" have an average particle diameter of about 400 µm or less, in order that roughness is not felt in the mouth. Preferably, the average particle diameter of the fine granules is 300 to 400 µm.

Aside from the average particle diameter of the above "fine granules", regarding the maximum particle size, the particle diameter is practically 425 µm or less, and preferably practically 400 µm or less. Preferably, the particle diameter is practically 300 to 425 µm, more preferably 300 to 400

"Practically" as used in "the particle diameter is practically 425 µm or less" and "the particle diameter is practically 400 µm or less" means that the particles may include a small quantity (about 5 weight % or less) of particles whose particle diameter is out of above described range, to include the inevitably contaminant particles.

"An acid-labile physiologically active substance" includes a compound being unstable in an acidic region and/or a compound inactivated by an acid, especially a pharmaceutical ingredient. Concretely mentioned are vitamins such as vitamin $B_{12}$, fursultiamine, folic acid, vitamin A, vitamin D, as well as a known benzimidazole compound having an antiulcer activity of the formula (I) below, or a salt thereof.

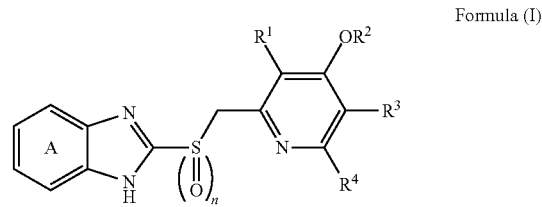

Formula (I)

wherein ring A may be substituted; $R^1$, $R^3$ and $R^4$ are the same or different and each is a hydrogen, an alkyl or an alkoxy; $R^2$ is $C_{1-4}$ alkyl which may be substituted by a substituent (s) selected from the group consisting of halogen, hydroxy and $C_{1-4}$ alkoxy; and n is 0 or 1.

In the above formula (I), "substituent(s)" of the "substituted ring A" include, for example, halogen, $C_{1-10}$ alkyl which may be substituted, $C_{3-7}$ cycloalkyl which may be substituted, $C_{2-16}$ alkenyl which may be substituted, $C_{1-10}$ alkoxy which may be substituted, cyano, carboxy, $C_{1-7}$ alkoxycarbonyl, $C_{1-4}$ alkoxycarbonyl-$C_{1-4}$ alkyl, carbamoyl, carbamoyl-$C_{1-4}$ alkyl, hydroxy, hydroxy-$C_{1-7}$ alkyl, $C_{1-6}$ acyl, carbamoyloxy, nitro, $C_{2-6}$ acyloxy, $C_{6-12}$ aryl, $C_{6-12}$ aryloxy, $C_{1-6}$ alkylthio, $C_{1-6}$ alkylsulfinyl, etc.

The "substituent" of the above "$C_{1-10}$ alkyl which may be substituted", "$C_{3-7}$ cycloalkyl which may be substituted", or "$C_{2-16}$ alkenyl which may be substituted" includes, for example, (1) halogen, (2) nitro, (3) amino which may be substituted by 1 or 2 of $C_{1-4}$ alkyl and $C_{1-4}$ acyl, etc., (4) amidino, (5) guanidino, (6) carbamoyl, etc. The number of these substituent is 1 to 3.

The "substituent" of the above "$C_{1-10}$ alkoxy which may be substituted" includes, for example, (1) halogen, (2) nitro, (3) amino which may be substituted by 1 or 2 of $C_{1-4}$ alkyl and $C_{1-4}$ acyl, etc., (4) amidino, (5) guanidino, etc. The number of these substituent is 1 to 3.

The above "$C_{1-6}$ acyl" includes, for example, $C_{2-6}$ alkanoyl such as formyl, acetyl, propionyl, etc.

The above "$C_{1-4}$ acyl" includes, for example, formyl and $C_{2-4}$ alkanoyl such as acetyl, propionyl, etc.

The above "$C_{2-6}$ acyloxy" includes, for example, $C_{2-6}$ alkanoyloxy such as acetyloxyl, etc.

The above "$C_{6-12}$ aryl" includes, for example, phenyl, naphthyl, etc.

The above "$C_{6-12}$ aryloxy" includes, for example, phenoxy, naphthyloxy, etc.

The "alkyl" for $R^1$, $R^3$ or $R^4$ includes, for example, a straight-chain or branched $C_{1-10}$ alkyl such as methyl, ethyl, n-propyl, isopropyl, n-butyl, isobutyl, sec-butyl, tert-butyl, n-pentyl, isopentyl, neopentyl, hexyl, heptyl, octyl, nonyl, decyl, etc. Among others, preferred is a straight-chain or branched $C_{1-6}$ alkyl. More preferred is a straight-chain or branched $C_{1-3}$ alkyl.

The "alkoxy" for $R^1$, $R^3$ or $R^4$ includes, for example, $C_{1-10}$ alkoxy such as methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy, cyclohexyloxy, etc. Among others, preferred is $C_{1-6}$ alkoxy. More preferred is $C_{1-3}$ alkoxy.

The "$C_{1-4}$ alkyl" of the "$C_{1-4}$ alkyl which may be substituted by a substituent(s) selected from the group consisting of halogen, hydroxy, and $C_{1-4}$ alkoxy" for $R^2$ includes, for example, methyl, ethyl, n-propyl, isopropyl, n-butyl, isobutyl, sec-butyl, tert-butyl, etc.

The "$C_{1-4}$ alkoxy" of the above "$C_{1-4}$ alkyl which may be substituted by a $C_{1-4}$ alkoxy" includes, for example, methoxy, ethoxy, n-propoxy, isopropoxy, n-butoxy, isobutoxy, sec-butoxy, tert-butoxy, etc.

The number of the substituents which the "$C_{1-4}$ alkyl" has is preferably 1 to 3.

Salts of the benzimidazole compound include pharmaceutically acceptable salts such as alkali metal salts, e.g., sodium salts and potassium salts, alkaline earth metal salts e.g., calcium salts and magnesium salts, etc.

Such benzimidazole compounds having an antiulcer activity, or salts thereof include, for example, a compound or a salt thereof disclosed in JP-A-52-62275, JP-A-54-141783, JP-A-57-53406, JP-A-58-135881, JP-A-58-192880, JP-A-59-181277, JP-A-61-50978, JP-A-62-116576, JP-A-62-277322, JP-A-62-258320, JP-A-62-258316, JP-A-64-6270, JP-A-64-79177, JP-A-5-59043, JP-A-62-111980, JP-A-5-117268, EP-A-166287, EP-A-519365, and so forth.

The "physiologically active substance" of the present invention preferably is a benzimidazole compound or a salt thereof such as lansoprazole, omeprazole, rabeprazole, pantoprazole, perprazole, leminoprazole, TU-199, etc. Preferred is lansoprazole and omeprazole, etc. More preferred is lansoprazole.

The amount of the "acid-labile physiologically active substance" in the "composition" is, for example, about 10 weight % or more, preferably about 20 weight or more, more preferably about 23 weight % or more, especially preferably about 25 weight % or more. Among others, preferred is 20 to 50 weight %.

In the "composition", a basic inorganic salt is preferably incorporated with the acid-labile physiologically active substance.

The "basic inorganic salt" includes, for example, a basic inorganic salt of sodium, potassium, magnesium and/or calcium, preferably a basic inorganic salt of magnesium and/or calcium. Among others, preferred is a basic inorganic salt of magnesium.

The basic inorganic salt of sodium includes, for example, sodium carbonate, sodium hydrogencarbonate, etc.

The basic inorganic salt of potassium includes, for example, potassium carbonate, potassium hydrogencarbonate, etc.

The basic inorganic salt of magnesium includes, for example, heavy magnesium carbonate, magnesium carbonate, magnesium oxide, magnesium hydroxide, magnesium metasilicate aluminate, magnesium silicate, magnesium aluminate, synthetic hydrotalcite [$Mg_6Al_2(OH)_{16}.CO_3.4H_2O$], aluminum magnesium hydroxide [$2,5MgO.Al_2O_3.xH_2O$], etc. Among others, preferred is heavy magnesium carbonate, magnesium carbonate, magnesium oxide, magnesium hydroxide, etc.

The basic inorganic salt of calcium includes, for example, precipitated calcium carbonate, calcium hydroxide, etc.

The preferable examples of the "basic inorganic salt" include heavy magnesium carbonate, magnesium carbonate, magnesium oxide, magnesium hydroxide, etc.

Such basic inorganic salt of magnesium or calcium, etc. has a basic pH (not less than 7) when it is in the form of a 1% aqueous solution or suspension.

Two or more of these basic inorganic salts (preferably a basic inorganic salt of magnesium, a basic inorganic salt of calcium, etc.) can be used as a mixture in a given ratio.

The amount of the basic inorganic salt to be used is appropriately selected depending on the kind of the basic inorganic salt and is, for instance, about 0.3 to 200 weight %, preferably about 1 to 100 weight %, more preferably about 10 to 50 weight %, especially preferably about 20 to 40 weight % relative to the benzimidazole compound or a salt thereof.

The "composition" may contain water-soluble polymers, the following binders, lubricants, and excipients, etc. in common use as pharmaceutical materials. The amount of such water-soluble polymers, binders, lubricants, and excipients is selected from amounts commonly employed in the manufacture of preparations in general dosage forms.

The "water-soluble polymer" includes, for example, a water-soluble polymer which is soluble in ethanol (i.e., an ethanol-soluble water-soluble polymer) such as a cellulose derivative (e.g., hydroxypropyl cellulose, which may be referred to as "HPC" hereinafter), poly(vinylpyrrolidone), etc.; a water-soluble polymer which is insoluble in ethanol (i.e., an ethanol-insoluble water-soluble polymer) such as a cellulose derivative (e.g., hydroxypropylmethyl cellulose, which may be referred to as "HPMC" hereinafter, methyl cellulose, carboxymethyl cellulose sodium, etc.), sodium polyacrylate, polyvinyl alcohol, sodium alginate, and guar gum, etc.

When such water-soluble polymers are used, the dissolution of drugs (physiologically active substances) can be controlled by employing them in combination with the ethanol-soluble water-soluble polymer and ethanol-insoluble water-soluble polymer or by employing them in combination with some water-soluble polymers having different viscosity.

In the present invention, the "water-soluble polymer" is preferably, a cellulose derivative such as HPC, HPMC, and methyl cellulose, and polyvinyl alcohol. More preferred is a cellulose derivative such as HPC, HPMC.

The "HPC" contains, for example, about 53.4 to 77.5 weight %, more preferably about 60 to 70 weight %, of hydroxypropoxyl group. The viscosity of 2 weight % aqueous solution of HPC at 20° C. is usually about 1 to 150,000 cps (centipoise). As the above HPC, hydroxypropyl cellulose defined in Japanese Pharmacopoeia may be employed. Hereinafter, all viscosity of HPC is a value of 2 weight % aqueous solution at 20° C.

The "HPMC" is a mixed ether which is connected by a methoxy group and a hydroxypropoxy group. The content of the methoxy group of HPMC is, for example, about 19 to 30 weight 4. The content of the hydroxypropoxy group is, for example, about 4 to 12 weight %. The viscosity of 2 weight % aqueous solution of HPMC at 20° C. is usually about 1 to 40,000 centistokes. As such HPMC may be employed hydroxypropylmethyl cellulose 2208 defined by Japanese Pharmacopoeia, hydroxypropylmethyl cellulose 2906 defined by Japanese Pharmacopoeia, hydroxypropylmethyl cellulose 2910 defined by Japanese Pharmacopoeia, and so forth. Hydroxypropyl cellulose(s) may be employed alone or in admixture of two or more thereof.

The content of the water-soluble polymer such as HPC and/or HPMC is usually about 0.1 to 50 weight %, preferably about 1 to 30 weight %, as against the whole "composition" containing the physiologically active substance, in order to control the dissolution of the physiologically active substance in the composition containing the physiologically active substance and retain a high content of the physiologically active substance.

The above "enteric coating layer" which coats the "composition having 10 weight % or more of an acid-labile physiologically active substance" includes, for example, an aqueous enteric polymer agent such as cellulose acetate phthalate (CAP), hydroxypropylmethyl cellulose phthalate (hereinafter, referred to as HP-55), hydroxymethyl cellulose acetate succinate, methacrylic acid copolymer [e.g., EUDRAGIT® L30D-55 etc. (trade name; methacrylic acid polymer dispersion; manufactured by Rohm GmbH (Germany)), KOLLICOAT MAE® 30DP (trade name; methacrylic acid/ethyl acrylate copolymers; manufactured by BASF (Germany)), Polyquid PA-30 (trade name; methacrylic acid/ethylacrylate copolymer dispersion; manufactured by SanyoKasei (Japan)), etc.], carboxymethyl cellulose, shellac, etc.; a sustained-release agent such as methacrylate copolymer [e.g., EUDRAGIT® NE30D (trade name; ethylacrylate/methyl methacrylate copolymer dispersion), EUDRAGIT® RL30D (trade name; ethyl acrylate/methyl methacrylate/methylacrylic acid ester copolymer), EUDRAGIT® RS30D (trade name; methyl acrylate/methyl methacrylate/methylacrylic acid ester copolymer), etc.]; a water-soluble polymer; plasticizers such as triethyl citrate, polyethylene glycol, acetylated monoglyceride, triacetin, castor oil, etc. and mixtures thereof.

The "aqueous enteric polymer agent" is preferably a methacrylate copolymer. The "sustained-release agent" is preferably a methacrylate copolymer.

The "sustained-release agent" is used in an amount of 5 to 30 weight %, preferably 5 to 15 weight %, relative to 100 weight % of the "aqueous enteric polymer agent". The "plasticizers" is used in an amount of 5 to 30 weight % relative to 100 weight % of the "aqueous enteric polymer agent".

The "additives" of the "orally disintegrable tablet which comprises (i) fine granules having an average particle diameter of 400 μm or less, which fine granules comprise a composition coated by an enteric coating layer, said composition having 10 weight % or more of an acid-labile physiologically active substance and (ii) an additive" may be ones commonly employed as pharmaceutical materials. The amount of such additives to be used is selected from amounts commonly employed in the manufacture of preparations in general dosage forms.

The "additives" include, for example, a water-soluble sugar alcohol, a crystalline cellulose, a low-substituted hydroxypropyl cellulose, as well as, binders, acids, foaming agents, artificial sweeteners, flavorants, lubricants, colorants, stabilizers, excipients, disintegrants, and so forth.

The "water-soluble sugar alcohol" means a water-soluble sugar alcohol which needs water in an amount of less than 30 ml when 1 g of water-soluble sugar alcohol is added to water and dissolved within about 30 minutes at 20° C. by strongly shaking every 5 minutes for 30 seconds.

The "water-soluble sugar alcohol" includes, for example, sorbitol, mannitol, maltitol, reduced starch saccharide, xylitol, reduced paratinose, erythritol, etc. Two or more of these water-soluble sugar alcohols can be used as a mixture in a given ratio.

The "water-soluble sugar alcohol" is preferably mannitol, xylitol and erythritol. More preferred is mannitol and erythritol. Especially preferred is mannitol. As erythritol, one that is produced by fermentation with yeasts using glucose as the starting material, and that has a particle size of at most 50 mesh is used. Such erythritol is available on the market, e.g. as manufactured by Nikken Chemical Co., Ltd. (Japan).

The "water-soluble sugar alcohol" is usually employed in an amount of about 5 to 97 weight %, preferably about 10 to 90 weight % relative to 100 weight % of the orally disintegrable tablet apart from the fine granules, in order to obtain sufficient strength of the preparation and sufficient disintegration or dissolution in the oral cavity.

For example, mannitol or erythritol is usually employed in an amount of about 5 to 90 weight %, preferably about 10 to 80 weight %, more preferably about 20 to 80 weight %, especially preferably about 50 to 80 weight % relative to 100 weight % of the orally disintegrable tablet apart from the fine granules.

The "crystalline cellulose" includes refined one having partially α-cellulose depolymerization. Such crystalline cellulose includes one called microcrystalline cellulose. Examples of the "crystalline cellulose" include CEOLUS KG801, avicel PH101, avicel PH102, avicel PH301, avicel PH302, avicel RC-591 (crystalline cellulose carmellose sodium), etc. Among these, preferably employed is CEOLUS KG801 which is also called crystalline cellulose of high compressibility. Two or more of the crystalline cellulose can be used as a mixture in a given ratio. Such crystalline cellulose is available on the market, for example, as manufactured by Asahi Chemical Co., Ltd. (Japan).

The "crystalline cellulose" is used, for instance, in an amount of about 3 to 50 weight %, preferably about 5 to 40 weight %, more preferably about 5 to 20 weight % relative to 100 weight % of the orally disintegrable tablet apart from the fine granules.

The "low-substituted hydroxypropyl cellulose" means a low-substituted hydroxypropyl cellulose wherein the content of hydroxypropoxyl group in the hydroxypropyl cellulose (hereinafter, may be abbreviated to "the content of HPC group") is about 5.0 to 9.9 weight %, preferably a low-substituted hydroxypropyl cellulose wherein the content of HPC group is about 5.0 to 7.0 weight %, a low-substituted hydroxypropyl cellulose wherein the content of HPC group is about 7.0 to 9.9 weight %, and so forth.

The "low-substituted hydroxypropyl cellulose wherein the content of HPC group is about 7.0 to 9.9%" includes, for example, LH-22, LH-32 and mixtures thereof, which are commercially available [Shin-Etsu Chemical Co., Ltd. (Japan)]. Also, they can be produced in accordance with per se known methods, for example, methods described in JP-B-82 53100 or analogous thereto.

The low-substituted hydroxypropyl cellulose wherein the content of HPC group is about 5.0 to 7.0% includes, for example, LH-23, LH-33 and mixtures thereof, described in the following Reference Examples. They can be produced in accordance with per se known methods, for example, methods described in JP-B-82 53100 or analogous thereto.

At first, alkaline cellulose containing free alkaline and propylene oxide is reacted to obtain the crude low-substituted hydroxypropyl cellulose containing free alkaline.

Concretely, for example, raw material pulp such as wood pulp and cotton leader is immersed in about 10 to 50% concentration of an aqueous solution of sodium hydroxide, and pressed to obtain alkaline cellulose of which NaOH/cellulose ratio is about 0.1 to 1.2 (ratio by weight). Next, crude low-substituted hydroxypropyl cellulose containing free alkaline is obtained by reacting the resulting alkaline cellulose and propylene oxide with stirring at about 20 to 90° C. for about 2 to 8 hours. Propylene oxide is used in an amount so that the content of hydroxypropoxyl group in the desired low-substituted hydroxypropyl cellulose can be 5 or more weight % to less than 7 weight % (in case of the low-substituted hydroxypropyl cellulose wherein the content of HPC group is about 5.0 to 7.0 weight %), 7 or more weight % to less than 9.9 weight % (in case of the low-substituted hydroxypropyl cellulose wherein the content of HPC group is about 7.0 to 9.9 weight %).

The crude low-substituted hydroxypropyl cellulose containing free alkaline is dispersed in water or hot water containing about 5 to 80% of acid necessary to neutralize all the alkaline, and a part of the crude low-substituted hydroxypropyl cellulose containing free alkaline is dissolved therein. Acid is further added to neutralize the remaining alkaline.

After the neutralization, some processes such as drainage, drying and grinding are performed in accordance with conventional methods to obtain the desired low-substituted hydroxypropyl cellulose.

The particle diameter of "the low-substituted hydroxypropyl celluloses wherein the content of hydroxypropoxyl group is 5.0 to 7.0 weight %" to be used in the present invention is, for example, about 5 to 60 μm, preferably about 10 to 40 μm, as a average particle diameter.

In the above ranges, in case that low-substituted hydroxypropyl celluloses (L-HPC) having a relatively large particle diameter (for example, L-HPC having about 26 to 40 tun of the average particle diameter) is employed, a pharmaceutical preparation superior in disintegrability can be produced. On the other hand, in case that L-HPC having a relatively small particle diameter (for example, L-HPC having about 10 to 25 μm of the average particle diameter) is employed, a pharmaceutical preparation superior in strength of the preparation can be produced. Accordingly, the particle diameter of L-HPC can be suitably selected according to the characteristics of the desired pharmaceutical preparation.

The "low-substituted hydroxypropyl cellulose wherein the content of HPC group is 5.0 to 7.0 weight %" or the "low-substituted hydroxypropyl cellulose wherein the content of HPC group is 7.0 to 9.9%" is usually employed in an amount of about 3 to 50 weight %, preferably about 5 to 40 weight %, relative to 100 weight % of the orally disintegrable tablet apart from the fine granules, in order to obtain sufficient oral disintegrability and sufficient strength of the preparation.

The "binders" include, for example, hydroxypropyl cellulose, hydroxypropylmethylcellulose, crystalline cellulose, a starch (pregelatinized starch), polyvinylpyrrolidone, gum arabic, powder, gelatin, pullulan, low-substituted hydroxypropyl cellulose, etc. The use of crystalline cellulose as the binders provides a solid preparation which exhibits more excellent strength of a preparation while retaining excellent disintegration and dissolution in the oral cavity.

The "acids" include, for example, citric acid (e.g., citric acid anhydrous), tartaric acid, malic acid, etc.

The "foaming agents" include, for example, sodium hydrogen carbonate, etc.

The "artificial sweeteners" include, for example, saccharin sodium, dipotassium glycyrrhizinate, aspartame, stevia, thaumatin, etc.

The "flavorants" include synthetic flavorants or natural flavorants, such as lemon, lime, orange, menthol, strawberry, etc.

The "lubricants" include, for example, magnesium stearate, sucrose fatty acid ester, polyethyleneglycol, talc, stearic acid, etc.

The "colorants" include, for example, various food colorants such as Food Yellow No. 5, Food RED No. 2, Food Blue No. 2, etc., food lakes, red iron oxide, etc.

The "stabilizers" include, for example, the above-mentioned "basic inorganic salt".

The "excipients" include, for example, lactose, sucrose, D-mannitol, starch, corn starch, crystalline cellulose, light silicic anhydride, titanium oxide, etc.

The "disintegrants" include those conventionally used in the pharmaceutical field, such as (1) crospovidone, (2) super disintegrants such as croscarmellose sodium [FMC-Asahi Chemical Co., Ltd. (Japan)], carmellose calcium [Gotoku Chemical(Yakuhin), (Japan)], (3) carboxymethylstarch sodium [e.g., Matsutani Chemical Co., Ltd. (Japan)], (4) low-substituted hydroxypropyl cellulose [e.g., Shin-Etsu Chemical Co., Ltd. (Japan)], (5) corn starch, etc. Among others, preferred is, for example, crospovidone.

The "crospovidone" includes polyvinylpolypyrrolidone (PVPP), 1-vinyl-2-pyrrolidinone homopolymer, 1-ethenyl-2-pyrrolidinone homopolymer, etc. such as Kollidon CL [manufactured by BASF (Germany)], Polyplasdone XL [manufactured by ISP Ltd. (Japan)], Polyplasdone XL-10 [manufactured by ISP Ltd. (Japan)], Polyplasdone INF-10 [manufactured by ISP Ltd. (Japan)], etc. Usually crospovidone having a molecular weight of at least 1,000,000 is used.

Two or more of these disintegrants can be as a mixture in a given ratio. For example, (i) crospovidone solely, or (ii) crospovidone and another disintegrants) is preferably employed.

The "disintegrants" are used, for instance, in an amount of about 1 to 15 weight %, preferably about 1 to 10 weight %, more preferably about 3 to 7 weight %, relative to 100 weight % of the orally disintegrable tablet apart from the fine granules.

In the present invention, the "fine granules" may contain, for example, titanium oxide as a masking agent.

The diameter of the "orally disintegrable tablet" of the present invention is about 5 to 20 mm, preferably about 7 to 15 mm, more preferably about 8 to 13 mm.

The "orally disintegrable tablet" may comprise no lubricant inside the tablet.

The "orally disintegrable tablet" of the present invention exhibits fast disintegrability or dissolubility in the oral cavity, and also an appropriate strength of preparation.

The oral disintegration time of the "orally disintegrable tablet" of the present invention (the time for healthy male or female adults to complete disintegration by buccal saliva) is one minute or less, usually about 50 seconds or less, preferably about 40 seconds or less, more preferably about 30 seconds or less.

The strength of the "orally disintegrable tablet" of the present invention (measurement with a tablet hardness tester) is usually about 1 to 20 kg, preferably about 2 to 15 kg, more preferably 3 to 8 kg.

In the above-mentioned fine granules, "fine granules having an average particle diameter of 400 μm or less, which comprise a composition coated by an enteric coating layer, said composition having (1) 25 weight % or more of an acid-labile physiologically active substance and (ii) a basic inorganic salt" are novel.

The "fine granules" have an average particle diameter of about 400 μm or less, preferably 350 μm or less. Preferably, the average particle diameter of the fine granules is 300 to 400 μm. Aside from the average particle diameter of the "fine granules", regarding the maximum particle size, the particle diameter is practically 425 μm or less, and preferably practically 400 μm or less. Preferably, the particle diameter is practically 300 to 400 μm or less.

Regarding the fine granule of the present invention, the dissolution of the physiologically active substance can be controlled by formulating the coat (coating layer) to have different viscosity or content of the water-soluble polymer (e.g., HPC, HPMC and so forth) or by formulating the coat to have a controlled ratio of the ethanol-soluble water-soluble polymer (e.g., HPC) and the ethanol-insoluble water-soluble polymer (e.g., HPMC). The dissolution of the physiologically active substance is not very influenced by liquidity, which can be suitably controlled.

As a pharmaceutical preparation which comprises the "fine granules" of the present invention, there may be employed, for example a solid preparation such as tablet, granule, fine granule, capsule, effervescent, etc; a liquid preparation such as suspension preparation, etc. Among others, preferred is a tablet, more preferred is an orally disintegrable tablet.

When the "fine granule" of the present invention is used for a tablet except for an orally disintegrable tablet, the diameter of the tablet is about 5 to 10 mm, preferably about 5 to 8 mm. When the fine granule of the present invention is used for a capsule, the size of the capsule is preferably a #2 capsule or less.

The "orally disintegrable tablet" of the resent invention and the "pharmaceutical preparation which comprises the fine granules of the present invention" may contain a foaming component to impart a refreshing feeling at administration. Also, with an effervescent comprising the foaming component, the dissolution can be precisely controlled compared to the case of a fine granule alone. As the foaming component, various compounds can be employed as long as safety is not interfered with. Examples of the foaming component include alkaline metal carbonate (e.g., sodium carbonate, potassium carbonate, etc.), alkaline metal hydrogencarbonate (e.g., sodium hydrogencarbonate, potassium hydrogencarbonate, etc.) and ammonium carbonate and so forth. The foaming component(s) may be employed alone or in an admixture of two or more thereof. The preferable foaming component includes sodium carbonate, sodium hydrogencarbonate, ammonium carbonate and so forth. The ratio of the foaming component can be selected within the range in which it is possible to impart the foam, for example, about 10 to 2500 weight %, preferably about 50 to 2000 weight % (e.g., about 75 to 1500 weight %), more preferably about 100 to 1000 weight %, relative to 100 weight % of the fine granule.

In employing the effervescent and the fine granule having small particle diameter, it is advantageous to quickly prepare a homogeneous aqueous solution or suspension, and to maintain the dispersed condition. But, in case that the particle diameter is too small, the problem tends to occur that the fine granule adheres to the wall of machine by static electricity during production processes.

The specific volume of the above fine granule is about 3 ml/g or less, preferably about 2 ml/g or less. In order to maintain the homogeneous condition of the fine granule in the suspension obtained by adding the foaming agent composition, the specific volume can be suitably selected in the above range according to the specific gravity (specific volume) of the dispersion medium.

The "composition" in the present invention can be produced by a known granulation method.

The "granulation method" includes, for example, rolling granulation method (e.g., centrifugal rolling granulation, etc.), fluidized-bed granulation (e.g., rolling fluidized-bed granulation, fluidized granulation, etc.), stirring granulation and so forth. Among others, preferred is fluidized-bed granulation method, more preferred is rolling fluidized-bed granulation method.

Concrete example of the "rolling granulation method" includes a method using "CF apparatus" manufactured by Freund Industrial Co., Ltd. (Japan) and so forth. Concrete examples of the "rolling fluidized-bed granulation method" include methods using "SPIR-A-FLOW", "multi plex" manufactured by Powrex Corp. (U.S.A.), "New-Marumerizer" manufactured by Fuji Paudal Co., Ltd. (Japan), and so forth. The method for spraying the mixture can be suitably selected in accordance with the kind of granulator, and may be, for example, any one of a top spray method, a bottom spray method, a tangential spray method, and so forth. Among others, a tangential spray method is preferred.

The "composition" in the present invention can be produced in accordance with, for example, a method which comprises coating a core comprising crystalline cellulose and lactose with an acid-labile physiologically active substance.

For example, employed is a method described in JP-A-5-92918 (coating method), which comprises coating a core comprising crystalline cellulose and lactose with an acid-labile physiologically active substance, if necessary together with a basic inorganic salt, binders, lubricants, excipients, a water-soluble polymer, etc. (hereinafter, may be abbreviated to "coating layer"). For example, employed is a method which comprises coating a core with an acid-labile physiologically active substance and a basic inorganic salt, and then further with binders, lubricants, excipients, a water-soluble polymer, etc.

The average particle diameter of the "cores" is about 250 μm or less, preferably about 50 to 250 μm, more preferably about 100 to 250 μm, especially preferably about 100 to 200 μm. The "cores" having the above average particle diameter include particles which all pass through a #50 sieve (300 μm), particles where about 5 w/w % or less of the total remain on a #60 sieve (250 μm), and particles where about 10 w/w % or less of the total pass through a #282 sieve (53 μm). The specific volume of the "core" is about 5 ml/g or less, preferably about 3 ml/g or less.

Examples of the "core" include (1) a spherical granulated product comprising crystalline cellulose and lactose, (2) a spherical granulated product being about 150 to 250 μm and comprising crystalline cellulose (avicel SP, manufactured by Asahi Chemical Co., Ltd. (Japan)), (3) a stirring granulated product being about 50 to 250 μm and comprising lactose (9 parts) and α starch (1 part), (4) a micro particle being about 250 μm or less classified as a spherical granule comprising micro crystalline cellulose described in JP-A-61-213201, (5) a processed product such as wax formed to a sphere by spraying or melting granulation, (6) a processed product such as gelatin beads comprising oil component, (7) calcium silicate, (8) starch, (9) a porous particle such as chitin, cellulose, chitosan, etc, and (10) a bulk product such as granulated sugar, crystalline lactose or sodium chloride, and processed preparations thereof. Further, these cores may be produced in accordance with per se known grinding method or granulation method, and sifted to prepare the particles having the desired particle diameter.

The above "spherical granulated product comprising crystalline cellulose and lactose" includes, for example (i) a spherical granulated product being 100 to 200 μm and comprising crystalline cellulose (3 parts) and lactose (7 parts) [e.g., Nonpareil 105 (70-140) (particle diameter of 100 to 200 μm), manufactured by Freund Industrial Co., Ltd. (Japan)], (ii) a spherical granulated product being about 150 to 250 μl and comprising crystalline cellulose (3 parts) and lactose (7 parts) [e.g., Nonpareil NP-7:3, manufactured by Freund Industrial Co., Ltd. (Japan)], (iii) a spherical granulated product being 100 to 200 µm and comprising crystalline cellulose (4.5 parts) and lactose (5.5 parts) [e.g., Nonpareil 105T (70-140) (particle diameter of 100 to 200 µm), manufactured by Freund Industrial Co., Ltd. (Japan)], (iv) a spherical granulated product being about 150 to 250 µm and comprising crystalline cellulose (5 parts) and lactose (5 parts) [e.g., Nonpareil NP-5:5, manufactured by Freund Industrial Co., Ltd. (Japan)], and so forth.

In order to produce a pharmaceutical preparation which is superior in dissolution while retaining suitable strength, the "core" includes, for example, preferably the spherical granulated product comprising crystalline cellulose and lactose, more preferably the spherical granulated material comprising crystalline cellulose and lactose and containing 50 weight % or more of lactose. Among others, preferred is a core comprising 40 to 50 weight % of crystalline cellulose and 50 to 60 weight % of lactose.

As the "core" employed in the present invention, in particular, there may be employed the spherical granulated product comprising crystalline cellulose and lactose, more preferably the spherical granulated product with a diameter of about 100 to 200 µm and comprising crystalline cellulose (4.5 parts) and lactose (5.5 parts).

The "core" may contain the physiologically active substance such as the above described pharmaceutical ingredient. Also, the "core" may not contain the physiologically active substance because the release of the physiologically active substance can be controlled by a coating layer containing the physiologically active substance.

The "core" is preferably as uniform a sphere as possible, for reducing the irregularity of the coating, in addition to being a powdery core.

The ratio of the "coating layer" to the "core" can be selected within the range in which it is possible to control dissolution of the physiologically active substance and particle size of the composition, for example, usually about 50 to 400 weight % relative to 100 weight % of the core.

The coating layer may be constructed by plural layers. At least one layer of the plural layers must contain the physiologically active substance. The combination of various layers such as a coating layer not containing the active ingredient, abase coating layer, and an enteric coating layer which constitute the coating layer can be suitably selected.

In case that the "core" is coated, for example, the above physiologically active substance and the water-soluble polymer can be employed in admixture thereof. The admixture may be a solution or a dispersion, and can be prepared by using an organic solvent such as water or ethanol or an admixture thereof.

The concentration of the water-soluble polymer in the admixture varies according to the ratio of the physiologically active substance and the excipients, and is usually about 0.1 to 50 weight %, preferably about 0.5 to 10 weight %, in order to retain the binding strength of the physiologically active substance to the core and maintain the viscosity of the mixture so as not to reduce the workability.

Where the coating layer comprises plural layers, the concentration of the physiologically active substance in each layer may be changed successively or gradually by selecting for the content ratio or viscosity of the water-soluble polymer or by successive coating with mixtures varying in the ratio of the physiologically active substance and the other excipients. In the above case, it may be coated with a mixture in which the content ratio of the water-soluble polymer is out of the range of about 0.1 to 50 weight %, as long as the coating layer as a whole contains about 0.1 to 50 weight of the water-soluble polymer. Further, in forming the inactive coat according to known methods, the coating layer may comprise some layers such that the inactive layer may block each layer containing the physiologically active substance.

Also, in case of two or more physiologically active substances not suited in the compatibility, the core may be coated by employing each mixture together or separately.

The above coated material is dried, and passed through sieves to obtain a "composition" having uniform size. Because the form of the powder is usually according to the core, a fine granule being in the form of a rough sphere may be obtained. As the sieve may be employed, for example a #50 circular sieve (300 µm). The composition is obtained by selecting those which pass through the #50 circular sieve.

The "fine granule" in the present invention can be produced in accordance with in the same manner as above granulation method, for example, a method which comprises coating the composition with an enteric coating layer, in order to protect the acid-labile physiologically active substance or to impart enteric dissolution. If necessary, the composition coated with an enteric coating layer may be further coated by a water-soluble sugar alcohol, preferably mannitol. In such case, the strength of the orally disintegrable tablet comprising fine granules is improved.

The "enteric coating layer" is preferably a layer having about 20 to 70 µm, preferably about 30 to 50 µm of thickness and coating the whole surface of the composition containing the physiologically active substance. Accordingly, the smaller particle diameter of the composition, the higher the weight % of the enteric coating layer in the whole fine granule. In the fine granule of the present invention, the "enteric coating layer" is about 30 to 70 weight %, preferably about 50 to 70 weight %, of the fine granule as a whole.

The "enteric coating layer" may be constructed by plural (e.g., 2 or 3) layers. For example, employed is a method which comprises coating a composition with an enteric coating layer having polyethyleneglycol, and then with an enteric coating layer having triethyl citrate, followed by being coated with an enteric coating layer having polyethyleneglycol.

The "orally disintegrable tablet" of the present invention can be produced in accordance with a conventional method in the pharmaceutical field. Such methods include, for instance, a method which comprises blending the "fine granules" and the "additives", and molding, if necessary followed by drying. Concretely mentioned is a method which comprises blending the fine granules and the additives, if necessary with water, and molding, if necessary followed by drying.

The "blending procedure" can be carried out by any of the conventional blending techniques such as admixing, kneading, granulating, etc. The above "blending procedure" is carried out, for instance, by using an apparatus such as Vertical Granulator GV10 [manufactured by Powrex Corp. (Japan)], Universal Kneader [manufactured by Hata Iron Works Co., Ltd. (Japan)], fluidized bed granulator LAB-1 and FD-3S [manufactured by Powrex Corp. (Japan)], V-shape mixer, tumbling mixer, and so forth.

Preferred example of the method for the "orally disintegrable tablet" of the present invention is a method which comprises:
(i) coating a core comprising crystalline cellulose and lactose with an acid-labile physiologically active substance and a basic inorganic salt, followed by being coated with a coating layer comprising a water-soluble polymer to obtain a composition, (ii) coating the resultant composition with an enteric coating layer having polyethyleneglycol, and then with an enteric coating layer having triethyl citrate, and then with an enteric coating layer having polyethyleneglycol, followed by being coated by mannitol to obtain fine granule, and
(iii) blending the resultant fine granule with an additive, followed by molding.

Where the pharmaceutical preparation of the present invention, especially an orally disintegrable tablet, is one which comprises no lubricant inside the preparation or tablet, such preparation can be preferably produced in accordance with methods described in JP-A-56-14098, Japanese Patent No. 2681601, etc. Such preparation, especially an orally disintegrable tablet, has sufficient strength. The above lubricant includes, for example, magnesium stearate, sucrose fatty acid ester, polyethyleneglycol, talc, stearic acid, etc.

The pharmaceutical preparations such as solid preparation (e.g., tablets, granules, fine granules, capsules, effervescents, etc.) and liquid preparation such as suspending preparation, which comprises the "fine granules" of the present invention can be produced in accordance with a conventional method.

The solid pharmaceutical preparation containing the "fine granules" of the present invention and the "orally disintegrable tablet" of the invention can also be produced by the wet tabletting method. As the above method, it is preferably employed the methods described in JP-A-5-271054 and so forth. They can also be produced by drying after humidification. As the above method, preferably employed are the methods described in JP-A-9-48726, JP-A-8-291051 and so forth. Namely, it is effective to humidify before tabletting or after tabletting and then to dry, in order to enhance the hardness.

The "molding procedure" can be carried out, for instance, by tabletting with a pressure of 0.5 to 3 ton/cm$^2$, preferably 1 to 2 ton/cm$^2$ by using a single-punch tabletting machine [Kikusui Seisakusho (Japan)] or a rotary type tabletting machine [Kikusui Seisakusho (Japan)] when a solid preparation is a tablet, especially an orally disintegrable tablet.

The "drying procedure" can be carried out by any of the techniques used commonly in the art, such as vacuum drying, fluidized-bed drying, etc.

The "fine granules" of the invention can be used for a pharmaceutical preparation. The pharmaceutical preparation includes, for example, a solid preparation such as tablet, granule, fine granule, capsule, effervescent, etc.; a liquid preparation such as a suspension preparation, etc. Among others, a tablet is preferred. Such tablet preferably has suitable strength so as to be stable through production processes and distributions.

A solid pharmaceutical preparation comprising the fine granule of the invention is used for an orally disintegrable tablet and can be administered without water or together with water.

As administration methods, there are listed (1) a method of administration by dissolution or disintegration together with a little water, or without water and with saliva in the oral cavity, not to be swallowed as it is, or (2) a method of administration with water, where it is swallowed as it is. Also, the tablet may be administered dissolved or disintegrated with water.

The "orally disintegrable tablet" of the present invention is advantageously used in (a) cases where administration without water is necessary, (b) cases of administration to a patients who have difficulty in swallowing tablets, or (c) cases of administration to the aged or to children where there is a fear of blocking the throat if it is in usual tablet form.

In case of the above (a), the orally disintegrable tablet is preferably used for antipyretic agents, analgesic agents, anti-inflammatory agents, antianxiety drugs, antitussive-expectorants, anti motion sickness agents, drugs for prevention and treatment for car-sickness, and so forth.

In case of the above (b), the orally disintegrable tablet is preferably used for preventing and/or treating hypertension, hyperlipemia, diabetes, bronchial asthma, cerebrovascular diseases, and so forth.

The "orally disintegrable tablet" of the present invention and the pharmaceutical preparation which comprises the "fine granules" of the present invention can be safely administered orally to mammals such as mice, rats, rabbits, cats, dogs, bovines, horses, monkeys, humans, etc.

With the dosage of the "orally disintegrable tablet" of the present invention and the pharmaceutical preparation which comprises the "fine granules" of the present invention, varies depending on the pharmaceutically active ingredient, subject, kinds of diseases, etc., the dosage can be selected so that the dosage of the pharmaceutically active ingredient is an effective amount.

For instance, when a benzimidazole compound (I) or a salt thereof such as lansoprazole is employed as an acid-labile physiologically active substance, especially a pharmaceutically active ingredient, the "orally disintegrable tablet" of the present invention and the pharmaceutical preparation which comprises the "fine granules" of the present invention is useful for treatment and prevention of digestive ulcer (e.g., gastric ulcer, duodenal ulcer, anastomotic ulcer, Zollinger-Ellison syndrome, etc), gastritis, reflux esophagitis, etc.; eradication of H. pylori; suppression of gastrointestinal bleeding caused by digestive ulcer, acute stress ulcer and hemorrhagic gastritis; suppression of gastrointestinal bleeding caused by invasive stress (e.g., stress caused by cerebrovascular disease, head injury, failure of many organs, burn injury of a wide range, which necessitate a large-scale operation necessitating the following intensive management, or intensive care); treatment and prevention of ulcer caused by non-steroidal anti-inflammatory agent; treatment and prevention of gastric hyperacidity and ulcer caused by postoperative stress; administration before anesthesia, etc. The dosage of the preparation per an adult (body weight: 60 kg) is about 0.5 to 1,500 mg/day, preferably about 5 to 150 mg/day, as a benzimidazole compound (I) or a salt thereof such as lansoprazole.

The "orally disintegrable tablet" of the present invention and the pharmaceutical preparation which comprises the "fine granules" of the present invention can be administered once a day, or two or three times separately a day.

BEST MODE FOR CARRYING OUT THE INVENTION

The following Examples and Reference Examples are further illustrative but by no means limitative of the present invention.

Unless otherwise specifically indicated, the following "%" means weight %.

Also, the content of the hydroxypropoxyl group is measured in accordance with the methods described in Japanese Pharmacopoeia (13th edition).

The physical properties of the tablets and granules prepared in Examples were determined by the following test methods.

(1) Hardness Test

Determination was carried out with a tablet hardness tester [manufactured by Toyama Sangyo, Co. Ltd. (Japan)]. The test was performed in 10 μms and mean values were shown.

(2) Oral Disintegration Time

Time for complete disintegration only by saliva in the oral cavity was determined.

(3) Remaining Ratio

According to the 2nd method of the dissolution test defined in Japanese Pharmacopoeia, the dissolution test was performed by using 500 ml of 0.1N HCl (75 rpm) for 1 hour. Then, the enteric fine granule was collected by means of the sieve.

The content of the drug in the collected fine granule was measured by the HPLC method. The remaining ratio was calculated according to the following expression with the content of the drug in the tablet which is measured separately by HPLC method.

Remaining ratio=(Content of the drug in the collected fine granule after the dissolution test using 0.1N HCl for 1 hour)/(Content of the drug in the tablet)

(4) Acid-resistance: Dissolution Using 0.1N HCl

According to the 2nd method of the dissolution test defined in Japanese Pharmacopoeia, the dissolution test was performed by using 500 ml of 0.1N HCl (75 rpm) for 1 hour. Then, test medium was collected and filtered by using a 0.45 μm membrane filter. The absorbance was measured to calculate the dissolution of the drug into 0.1N HCl.

(5) Average Particle Diameter: Volume Based Distribution Median Diameter (Median Diameter: 50% Particle Diameter from Cumulative Distribution)

Determination was carried out with Raser Diffraction Analyzer, type: HEROS RODOS [trade name, manufactured by Sympatec (Germany)].

EXAMPLES

Example 1

(1) Production of Granules having a Core

A centrifugal fluidized coating granulator [manufactured by Powrex Corp. (Japan), MP-10 (Type 2)] is charged with 300 g of Nonpareil 105 (70-140) (particle diameter of 100 to 200 μm). With the inlet air temperature and the temperature of the loading being controlled at 85° C. and about 28° C. respectively, the Nonpareil is coated by spraying a bulk liquid of the following composition prepared in advance in accordance with the tangential spray method at a spray rate of 20 g/min. The spraying operation is stopped when the specified amount of the bulk liquid has been sprayed, and then drying is carried out in the granulator for 7 minutes. The resulting granules are sieved through a #60 circular sieve (250 μm) and a #100 circular sieve (150 μm) to provide 750 g of granules having a core.

Bulk Liquid:

| Lansoprazole | 300 g |
| Magnesium carbonate | 100 g |
| L-HPC | 50 g |
| HPC (Type SSL) | 100 g |
| Water | 1650 g |

(2) Production of Film-Undercoated Granules Having a Core

A centrifugal fluidized coating granulator [manufactured by Powrex Corp. (Japan), MP-10 (Type 2)] is charged with 680 g of the above granules having a core. With the inlet air temperature and the temperature of the loading being controlled at 70° C. and about 36° C., respectively, an undercoating liquid of the following composition prepared in advance is sprayed in accordance with the tangential spray method at a spray rate of 10 g/min. to provide 650 g of film-undercoated granules having a core.

Undercoating Liquid:

| HPMC (Type 2910, viscosity: 3 centistokes) | 32 g |
| Talc | 8 g |
| Water | 760 g |

(3) Production of Enteric Coated Granules having a Core

A centrifugal fluidized coating granulator [manufactured by Powrex Corp. (Japan), MP-10 (Type 2)] is charged with 450 g of the above film-undercoated granules having a core. With the inlet air temperature and the temperature of the loading being controlled at 65° C. and about 36° C., respectively, an enteric film coating liquid of the following composition prepared in advance is sprayed in accordance with the tangential spray method at a spray rate of 17 g/min. The coated powders are dried in vacuum at 40° C. for 16 hours, and sieved through a #42 circular sieve (355 μm) and a #80 circular sieve (177 μm) to provide 950 g of enteric coated granules having a core.

Enteric Film Coating Liquid:

| Eudragit L30D-55 | 1078.3 g |
| Eudragit NE30D | 138.5 g |
| Triethyl citrate | 46.0 g |
| Glyceryl monostearate | 23.1 g |
| Talc | 16.0 g |
| Polysorbate 80 | 9.0 g |
| Yellow iron oxide | 0.5 g |
| Water | 2038.5 g |

| Sieve | weight ratio |
| --- | --- |
| #18 (850 μm) on | 0% |
| #30 (500 μm) on | 0% |
| #200 (75 μm) on | 100% |
| #200 (75 μm) pass | 0% |

(4) Production of Granulated Powders

A fluidized bed granulator [manufactured by Powrex Corp. (Japan), LAB-1] is charged with 1321.2 g of erythritol [manufactured by Nikken Chemical Co., Ltd. (Japan)], 360.0 g of low-substituted hydroxypropyl cellulose LH-32 [hydroxypropoxyl group contents of 8.8%, manufactured by Shin-Etsu Chemical Co., Ltd. (Japan)], 18.0 g of citric acid anhydrous, and 1.8 g of aspartame, and granulation is carried out while spraying a solution which is prepared by dissolving 3.6 g of polyethylene glycol (PEG-6000) in 896.4 ml of purified water. The granules are dried to provide granulated powders. To the granulated powders are added 90.0 g of crospovidone and 5.4 g of magnesium stearate, which is admixed in a bag to give mixed powders.

(5) Production of Orally Disintegrable Tablets

Hereinafter, the above "enteric coated granules having a core" is referred to as "enteric coated powders".

200.0 g of the above enteric coated powders and 300.0 g of the above mixed powders are tabletted using Autograph (trade name; compressing force measurement apparatus) with a punch having a beveled edge, 11 mm in diameter, at a tabletting pressure of 1.0 ton/cm² to provide tablets each weighing 500 mg.

Reference Example 1

An alkaline cellulose comprising 24.1% of NaOH, 1.7% of $Na_2CO_3$, 42.9% of cellulose, 31.8% of $H_2O$ was obtained by immersing a wood pulp in 49% aqueous solution of sodium hydroxide and then by pressing it. A reactor was charged with 100 weight parts of the alkaline cellulose. Then, nitrogen gas replacement was carried out. After the replacement, 5 weight parts of propylene oxide was charged in the reactor and reacted with stirring at 40° C. for 1 hour, at 50° C. for 1 hour and at 70° C. for 1 hour to obtain 103 weight parts of a reactant.

On the other side, a kneader was charged with 2.5 weight parts of hot water at 65° C. and 0.13 weight parts of glacial acetic acid (about 40 weight % against equivalent for neutralization, initial neutralized acid) and therein, 1 weight part of the above resulting alkaline cellulose was dispersed. Then, the temperature was set at 30° C. to dissolve a part of the reactant, and 0.20 weight part of glacial acetic acid (the remainder of an equivalent for neutralization, complete neutralized acid) to obtain a processed fiber product containing a part of dissolution and a part of deposit.

The resulting product was washed with hot water at about 80° C., drained, dried, ground by means of a high rolling impact grinder, and sifted by means of a 100 mesh sieve to obtain the powder of low-substituted hydroxypropyl cellulose LH-33 (the content of hydroxypropoxyl group: 5.8 weight %, the average particle diameter: 17.8 μm).

Reference Example 2

Powders of low-substituted hydroxypropyl cellulose LH-23 (hydroxypropoxyl group contents: 5.7 weight %, average particle diameter: 30.8 μm) were obtained in the same manner as in Reference Example 1.

Example 2

(1) Production of Granules having a Core

A centrifugal fluidized coating granulator [manufactured by Powrex Corp. (Japan), MP-10 (Type 2)] was charged with 300 g of Nonpareil 105 [(trade name) particle diameter: 100 to 200 μm]. With the inlet air temperature and the temperature of the loading being controlled at 70° C. and about 30° C., respectively, the Nonpareil was coated by spraying a spray liquid of the following composition prepared in advance in accordance with the tangential spray method at a spray rate of 22 g/min., and then drying was carried out in the granulator for 10 minutes. The resulting granules were sieved through a #48 circular sieve (300 μm) and a #100 circular sieve (150 μm) to provide 2186 g of powders (150 to 300 μm) having a core.

Spray liquid:

| | |
|---|---|
| Lansoprazole | 927 g |
| Magnesium carbonate | 309 g |

| | |
|---|---|
| Low-substituted hydroxypropyl cellulose LH-32 (hydroxypropoxyl group contents: 8.8 wt %) (average particle diameter: 17.57 μm) | 154.5 g |
| Hydroxypropyl cellulose (Type SSL) | 309 g |
| Purified water | 3955 g |

(2) Production of Film-Undercoated Granules having a Core

A centrifugal fluidized coating granulator [manufactured by Powrex Corp. (Japan), MP-10 (Type 2)] was charged with 2040 g of the above granules having a core. With the inlet air temperature and the temperature of the loading being controlled at 75° C. and about 40° C., respectively, an undercoating liquid of the following composition prepared in advance was sprayed in accordance with the tangential spray method at a spray rate of 13 g/min. to provide 2145 g of film-undercoated granules having a core.

Undercoating Liquid:

| | |
|---|---|
| Hydroxypropylmethylcellulose (Type 2910, viscosity: 3 centistokes) | 264 g |
| Purified water | 5016 g |

(3) Production of Enteric Coated Granules having a Core

A centrifugal fluidized coating granulator [manufactured by Powrex Corp. (Japan), MP-10 (Type 2)] was charged with 1710 g of the above film-undercoated granules having a core. With the inlet air temperature and the temperature of the loading being controlled at 70° C. and about 40° C., respectively, an enteric film coating liquid of the following composition prepared in advance was sprayed in accordance with the tangential spray method at a spray rate of 17 g/min., and dried for 7 minutes, and then sieved through a #42 circular sieve (355 μm) and a #80 circular sieve (177 μm) to provide 2393 g of enteric coated powders (177 to 355 μm) having a core.

Enteric Film Coating Liquid:

| | |
|---|---|
| Eudragit L30D-55 | 5016.4 g |
| Eudragit NE30D | 559.0 g |
| Triethyl citrate | 333.7 g |
| Glyceryl monostearate | 106.5 g |
| Polysorbate 80 | 34.8 g |
| Red iron oxide | 1.8 g |
| Purified water | 2547.1 g |

(4) Production of Enteric Coated and Mannitol Coated Granules having a Core

A centrifugal fluidized coating granulator [manufactured by Powrex Corp. (Japan), MP-10 (Type 2)] was charged with 600 g of the above enteric coated granules having a core. With the inlet air temperature and the temperature of the loading being controlled at 65° C. and about 32° C., respectively, an film coating liquid of the following composition prepared in advance was sprayed in accordance with the tangential spray method at a spray rate of 11 g/min., and then dried for 7 minutes to provide 617 g of enteric coated and mannitol coated granules having a core.

The average particle diameter of the obtained granules was 334.1 μm.

Film Coating Liquid:

| | |
|---|---|
| Mannitol | 33 g |
| Purified water | 297 g |

(5) Production of Mannitol-Granulated Powders

A fluidized bed granulator [manufactured by Powrex Corp. (Japan), LAB-1] was charged with 800 g of mannitol [manufactured by Merck Japan Co., Ltd.], and granulation was carried out while spraying 315 g of purified water. The granules were dried to provide 727.3 g of granulated powders.

(6) Production of Mixed Powders

To 97.3 g of the above mannitol-granulated powders were added 105 g of the above enteric coated and mannitol coated granules having a core, 15.0 g of low-substituted hydroxypropyl cellulose LH-33 (hydroxypropoxyl group contents: 5.8 weight %, average particle diameter: 17.8 μm), 22.5 g of crystalline cellulose [CEOLUS KG-801 (trade name), manufactured by Asahi Chemical Co., Ltd. (Japan)], 7.5 g of crospovidone, 1.5 g of citric acid anhydrous, 0.45 g of aspartame and 0.75 g of magnesium stearate, which was admixed in a bag to give mixed powders.

(7) Production of Orally Disintegrable Tablets 250.0 g of the above mixed powders were tabletted using Autograph (trade name; compressing force measurement apparatus) with a punch (15R), 11 mm in diameter, at a tabletting pressure of 1.5 ton/cm$^2$, to provide tablets each weighing 500 mg.

The hardness and oral disintegration time of each tablet thus obtained were 5.9 kg and 30 seconds, respectively.

Example 3

(1) Production of Granules having a Core

A centrifugal fluidized coating granulator [manufactured by Powrex Corp. (Japan), MP-10 (Type 2)] was charged with 900 g of Nonpareil 105 (trade name) (particle diameter of 100 to 200 μm). With the inlet air temperature and the temperature of the loading being controlled at 75° C. and about 29° C. respectively, the Nonpareil was coated by spraying a bulk liquid of the following composition prepared in advance in accordance with the tangential spray method at a spray rate of 22 g/min. The spraying operation was stopped when the specified amount 5654.7 g of the bulk liquid had been sprayed, and then drying was carried out in the granulator for 10 minutes. The resulting granules were sieved through a #60 circular sieve (250 μm) and a #100 circular sieve (150 μm) to provide 2424 g of granules having a core.

Bulk Liquid:

| | |
|---|---|
| Lansoprazole | 1080 g |
| Magnesium carbonate | 360 g |
| Low-substituted hydroxypropyl cellulose LH-32 (hydroxypropoxyl group contents: 8.8 weight %) | 180 g |
| Hydroxypropyl cellulose (Type SSL) | 360 g |
| Purified water | 4608 g |

(2) Production of Film-Undercoated Granules having a Core

A centrifugal fluidized coating granulator [manufactured by Powrex Corp. (Japan), MP-10 (Type 2)] was charged with 2337.5 g of the above granules having a core. With the inlet air temperature and the temperature of the loading being controlled at 80° C. and about 41° C., respectively, an undercoating liquid of the following composition prepared in advance was sprayed in accordance with the tangential spray method at a spray rate of 18 g/min. The spraying operation was stopped when the specified amount 6050 g of the undercoating liquid had been sprayed, and then drying was carried out in the granulator for 10 minutes to provide 2551 g of film-undercoated granules having a core.

Undercoating Liquid:

| | |
|---|---|
| Hydroxypropyl methylcellulose (Type 2910, viscosity: 3 centistokes) | 332.5 g |
| Low-substituted hydroxypropyl cellulose LH-32 (hydroxypropoxyl group contents: 8.8 weight %) (average particle diameter: 17.57 μm) | 17.5 g |
| Purified water | 6650 g |

(3) Production of Enteric Coated Granules having a Core

A centrifugal fluidized coating granulator [manufactured by Powrex Corp. (Japan), MP-10 (Type 2)] was charged with 570 g of the above film-undercoated granules having a core. With the inlet air temperature and the temperature of the loading being controlled at 75° C. and about 40° C., respectively, an enteric film coating liquid of the following composition prepared in advance was sprayed in accordance with the tangential spray method at a spray rate of 18 g/min. The spraying operation was stopped when the specified amount 2646 g of the enteric film coating liquid had been sprayed, and then drying was carried out in the granulator for 8 minutes. The coated powders were sieved through a #42 circular sieve (355 μm) and a #70 circular sieve (212 μm) to provide 1116 g of enteric coated granules having a core.

The average particle diameter of the obtained granules was 326.9 μm.

Enteric film coating liquid:

| | |
|---|---|
| Eudragit L30D-55 | 1911 g |
| Eudragit NE30D | 212.9 g |
| Triethyl citrate | 127.1 g |
| Glyceryl monostearate | 40.6 g |
| Polysorbate 80 | 13.3 g |
| Red iron oxide | 0.8 g |
| Purified water | 970.3 g |

(4) Production of Mixed Powders

To 200 g of the above enteric coated granules having a core were added 189.7 g of mannitol, 30.0 g of low-substituted hydroxypropyl cellulose LH-23 (hydroxypropoxyl group contents: 5.8 weight %, average particle diameter: 17.8 μm), 60.0 g of crystalline cellulose [CEOLUS KG-801 (trade name), manufactured by Asahi Chemical Co., Ltd. (Japan)], 15.0 g of crospovidone, 2.8 g of citric acid anhydrous and 25 g of magnesium stearate, which was admixed in a bag to give mixed powders.

(5) Production of Orally Disintegrable Tablets 250.0 g of the above mixed powders were tabletted using Autograph (trade name; compressing force measurement apparatus) with a punch (15R), 11 mm in diameter, at a tabletting pressure of 1.5 ton/cm$^2$, to provide tablets each weighing 500 mg.

The hardness and oral disintegration time of each tablet thus obtained were 4.2 kg and 24 seconds, respectively.

Example 4

(1) Production of Granules having a Core

A centrifugal fluidized coating granulator [manufactured by Powrex Corp. (Japan), MP-10 (Type 2)] was charged with 900 g of Nonpareil 105 (trade name) (particle diameter of 100 to 200 μm).

With the inlet air temperature and the temperature of the loading being controlled at 75° C. and about 32° C. respectively, the Nonpareil was coated by spraying a bulk liquid of the following composition prepared in advance in accordance with the tangential spray method at a spray rate of 20 g/min. The spraying operation was stopped when the specified amount 5654.7 g of the bulk liquid had been sprayed, and then drying was carried out in the granulator for 10 minutes. The resulting granules were sieved through a #48 circular sieve (300 μm) and a #100 circular sieve (150 μm) to provide 2280 g of granules having a core.

Bulk Liquid:

| | |
|---|---|
| Lansoprazole | 1080 g |
| Magnesium carbonate | 360 g |
| Low-substituted hydroxypropyl cellulose LH-32 (hydroxypropoxyl group contents: 8.8 weight %) | 180 g |
| Hydroxypropyl cellulose (Type SSL) | 360 g |
| Purified water | 4608 g |

(2) Production of Film-Undercoated Granules having a Core

A centrifugal fluidized coating granulator [manufactured by Powrex Corp. (Japan), MP-10 (Type 2)] was charged with 1020 g of the above granules having a core. With the inlet air temperature and the temperature of the loading being controlled at 85° C. and about 40° C., respectively, an undercoating liquid of the following composition prepared in advance was sprayed in accordance with the tangential spray method at a spray rate of 15 g/min. The spraying operation was stopped when the specified amount 1980 g of the undercoating liquid had been sprayed, and then drying was carried out in the granulator for 10 minutes to provide 1330.5 g of film-undercoated granules having a core.

Undercoating Liquid:

| | |
|---|---|
| Hydroxypropylmethylcellulose (Type 2910, viscosity: 3 centistokes) | 120 g |
| Titanium oxide (TiO$_2$) | 240 g |
| Sterilized Talc (trade name) [produced by Matsumura Sangyo Co. Ltd. (Japan)] | 240 g |
| Magnesium carbonate | 120 g |
| Purified water | 2880 g |

(3) Production of Enteric Coated Granules having a Core

A centrifugal fluidized coating granulator [manufactured by Powrex Corp. (Japan), MP-10 (Type 2)] was charged with 460 g of the above film-undercoated granules having a core. With the inlet air temperature and the temperature of the loading being controlled at 80° C. and about 41° C., respectively, an enteric film coating liquid of the following composition prepared in advance was sprayed in accordance with the tangential spray method at a spray rate of 13 g/min. The spraying operation was stopped when the specified amount 2205 g of the enteric film coating liquid had been sprayed.

Enteric Film Coating Liquid:

| | |
|---|---|
| Eudragit L30D-55 | 2290 g |
| Eudragit NE30D | 253 g |
| Triethyl citrate | 153 g |
| Glyceryl monostearate | 20 g |
| Polysorbate 80 | 8 g |
| Titanium oxide (TiO$_2$) | 53 g |
| Sterilized Talc H (trade name) [produced by Matsumura Sangyo Co. Ltd. (Japan)] | 53 g |
| Purified water | 2420 g |

(4) Production of Enteric Coated and Mannitol Coated Granules having a Core

Following (3), with the inlet air temperature and the temperature of the loading being controlled at 80° C. and about 35° C., respectively, an film coating liquid of the following composition prepared in advance was sprayed in accordance with the tangential spray method at a spray rate of 16 g/min. using a centrifugal fluidized coating granulator [manufactured by Powrex Corp. (Japan), MP-10 (Type 2)]. The spraying operation was stopped when the specified amount 824 g of the film coating liquid had been sprayed, and then drying was carried out in the granulator for 10 minutes. The resulting granules were sieved through a #42 circular sieve (355 pin) and a #60 circular sieve (250 μm) to provide 806 g of enteric coated and mannitol coated granules having a core.

The average particle diameter of the obtained granules was 326.6 pun.

Film Coating Liquid:

| | |
|---|---|
| Mannitol | 320 g |
| Purified water | 2880 g |

(5) Production of Mixed Powders

To 120 g of the above enteric coated and mannitol coated granules having a core were added 87.75 g of mannitol, 8.5 g of low-substituted hydroxypropyl cellulose LH-23 (hydroxypropoxyl group contents: 5.8 weight %), 4.5 g of low-substituted hydroxypropyl cellulose LH-33 (hydroxypropoxyl group contents: 5.8 weight %), 19.5 g of crystalline cellulose [CEOLUS KG-801 (trade name), manufactured by Asahi Chemical Co., Ltd. (Japan)], 6.5 g of crospovidone, 1.3 g of citric acid anhydrous, 1.3 g of aspartame and 0.65 g of magnesium stearate, which was admixed in a bag to give mixed powders.

(6) Production of Orally Disintegrable Tablets 250.0 g of the above mixed powders were tabletted using Autograph (trade name; compressing force measurement apparatus) with a punch (15R), 11 mm in diameter, at a tabletting pressure of 1.5 ton/cm$^2$, to provide tablets each weighing 500 mg.

The hardness and oral disintegration time of each tablet thus obtained were 3.9 kg and 20.5 seconds, respectively.

The remaining ratio of the obtained tablet after acid-resistance test was 97%.

Example 5

(1) Production of Granules having a Core

A centrifugal fluidized coating granulator [manufactured by Powrex Corp. (Japan), MP-10 (Type 2)] was charged with 900 g of Nonpareil 105 (trade name) (particle diameter of 100 to 200 μm). With the inlet air temperature and the temperature of the loading being controlled at 65° C. and about 30° C. respectively, the Nonpareil was coated by spraying a bulk liquid of the following composition prepared in advance in accordance with the tangential spray method at a spray rate of 22 g/min. The spraying operation was stopped when the specified amount 5661 g of the bulk liquid had been sprayed, and then drying was carried out in the granulator for 8 minutes. The resulting granules were sieved through a #42 circular sieve (350 μm) and a #100 circular sieve (150 μm) to provide 2074 g of granules having a core.
Bulk Liquid:

| | |
|---|---|
| Lansoprazole | 1080 g |
| Magnesium carbonate | 360 g |
| Low-substituted hydroxypropyl cellulose LH-32 (hydroxypropoxyl group contents: 8.8 weight %) | 180 g |
| Hydroxypropyl cellulose (Type SSL) | 360 g |
| Purified water | 4680 g |

(2) Production of Film-Undercoated Granules having a Core

A centrifugal fluidized coating granulator [manufactured by Powrex Corp. (Japan), MP-10 (Type 2)] was charged with 2074 g of the above granules having a core. With the inlet air temperature and the temperature of the loading being controlled at 78° C. and about 40° C., respectively, an undercoating liquid of the following composition prepared in advance was sprayed in accordance with the tangential spray method at a spray rate of 22 g/min. The spraying operation was stopped when the specified amount 1980 g of the undercoating liquid had been sprayed, and then drying was carried out in the granulator for 9 minutes. The resulting granules were sieved through a #42 circular sieve (350 μm) and a #100 circular sieve (150 μm) to provide 2555 g of film-undercoated granules having a core.
Undercoating Liquid:

| | |
|---|---|
| Hydroxypropylmethylcellulose (Type 2910, viscosity: 3 centistokes) | 252 g |
| Titanium oxide (TiO$_2$) | 108 g |
| Sterilized Talc (trade name) [produced by Matsumura Sangyo Co. Ltd. (Japan)] | 108 g |
| Low-substituted hydroxypropyl cellulose LH-32 (hydroxypropoxyl group contents: 8.8 weight %) | 180 g |
| Mannitol | 252 g |
| Purified water | 3600 g |

(3) Production of Enteric Coated Granules having a Core

A centrifugal fluidized coating granulator [manufactured by Powrex Corp. (Japan), MP-10 (Type 2)] was charged with 1320 g of the above film-undercoated granules having a core. With the inlet air temperature and the temperature of the loading being controlled at 80° C. and about 42° C., respectively, an enteric film coating liquid (A) of the following composition prepared in advance was sprayed in accordance with the tangential spray method at a spray rate of 22 g/min. The specified amount 1638 g of the enteric film coating liquid had been sprayed.
Enteric Film Coating Liquid (A):

| | |
|---|---|
| Eudragit L30D-55 | 1219.2 g |
| Eudragit NE30D | 134.4 g |
| Polyethylene glycol 6000 | 40.8 g |
| Glyceryl monostearate | 24.0 g |
| Polysorbate 80 | 7.2 g |
| Ferric oxide | 0.24 g |
| Ferric oxide (yellow) | 0.24 g |
| Citric acid anhydrous | 0.48 g |
| Purified water | 1693 g |

Following this, with the inlet air temperature and the temperature of the loading being controlled at 76° C. and about 42° C., respectively, an enteric film coating liquid (B) of the following composition prepared in advance was sprayed in accordance with the tangential spray method at a spray rate of 22 g/min. The specified amount 6552 g of the enteric film coating liquid had been sprayed.
Enteric Film Coating Liquid (B):

| | |
|---|---|
| Eudragit L30D-55 | 4032 g |
| Eudragit NE30D | 447.8 g |
| Triethyl citrate | 269.3 g |
| Glyceryl monostearate | 86.4 g |
| Polysorbate 80 | 25.9 g |
| Ferric oxide | 0.86 g |
| Ferric oxide (yellow) | 0.86 g |
| Citric acid anhydrous | 0.72 g |
| Purified water | 2624 g |

Following this, with the inlet air temperature and the temperature of the loading being controlled at 80° C. and about 42° C., respectively, an enteric film coating liquid (A) of the above mentioned composition prepared in advance was sprayed in accordance with the tangential spray method at a spray rate of 22 g/min. The specified amount 819 g of the enteric film coating liquid had been sprayed.

(4) Production of Enteric Coated and Mannitol Coated Granules having a Core

Following (3), with the inlet air temperature and the temperature of the loading being controlled at 85° C. and about 35° C., respectively, an film coating liquid of the following composition prepared in advance was sprayed in accordance with the tangential spray method at a spray rate of 22 g/min. using a centrifugal fluidized coating granulator [manufactured by Powrex Corp. (Japan), MP-10 (Type 2)]. The spraying operation was stopped when the specified amount 882 g of the film coating liquid had been sprayed, and then drying was carried out in the granulator for 10 minutes. The resulting granules were sieved through a #35 circular sieve (420 μm) and a #60 circular sieve (250 μm) to provide 1964 g of enteric coated and mannitol coated granules having a core.

The average particle diameter of the obtained granules was 333.7 μm.
Film Coating Liquid:

| | |
|---|---|
| Mannitol | 180 g |
| Purified water | 1080 g |

(5) Production of Mixed Powders

To 270 g of the above enteric coated and mannitol coated granules having a core were added 204.0 g of mannitol, 30 g of low-substituted hydroxypropyl cellulose LH-33 (hydroxypropoxyl group contents: 5.8 weight %), 30 g of crystalline cellulose [CEOLUS KG-801 (trade name), manufactured by Asahi Chemical Co., Ltd. (Japan)], 15 g of crospovidone, 3 g of citric acid anhydrous, 9 g of aspartame, 6 g of magnesium stearate and 3 g of flavor [STRAWBERRY DURAROME (trade name), manufactured by Nihon Filmenich Co., Ltd. (Japan)], which was admixed in a bag to give mixed powders.

(6) Production of Orally Disintegrable Tablets 570 g of the above mixed powders were tabletted using Autograph (trade name; compressing force measurement apparatus) with a punch having a beveled edge, 13 mm in diameter, at a tabletting pressure of 1.5 ton/cm$^2$, to provide tablets each weighing 570 mg.

The hardness and oral disintegration time of each tablet thus obtained were 2.6 kg and 20 seconds, respectively.

The acid-resistance of the obtained tablet was 3.5%.

Example 6

(1) Production of Granules Having a Core

A centrifugal fluidized coating granulator [manufactured by Powrex Corp. (Japan), MP-10 (Type 2)] was charged with 750 g of Nonpareil 105 (trade name) (particle diameter of 100 to 200 μm). With the inlet air temperature and the temperature of the loading being controlled at 65° C. and about 30° C. respectively, the Nonpareil was coated by spraying a bulk liquid of the following composition prepared in advance in accordance with the tangential spray method at a spray rate of 22 g/min. The spraying operation was stopped when the specified amount 4717.5 g of the bulk liquid had been sprayed, and then drying was carried out in the granulator for 8 minutes. The resulting granules were sieved through a #42 circular sieve (350 μl and a #100 circular sieve (150 μm) to provide 1811 g of granules having a core.

Bulk Liquid:

| | |
|---|---|
| Lansoprazole | 900 g |
| Magnesium carbonate | 300 g |
| Low-substituted hydroxypropyl cellulose LH-32 (hydroxypropoxyl group contents: 8.8 weight %) | 150 g |
| Hydroxypropyl cellulose (Type SSL) | 300 g |
| Purified water | 3900 g |

(2) Production of Film-Undercoated Granules having a Core

A centrifugal fluidized coating granulator [manufactured by Powrex Corp. (Japan), MP-10 (Type 2)] was charged with 1811 g of the above granules having a core. With the inlet air temperature and the temperature of the loading being controlled at 78° C. and about 38° C., respectively, an undercoating liquid of the following composition prepared in advance was sprayed in accordance with the tangential spray method at a spray rate of 22 g/min. The spraying operation was stopped when the specified amount 5274 g of the undercoating liquid had been sprayed, and then drying was carried out in the granulator for 9 minutes. The resulting granules were sieved through a #42 circular sieve (350 μm) and a #100 circular sieve (150 μm) to provide 2628 g of film-undercoated granules having a core.

Undercoating Liquid:

| | |
|---|---|
| Hydroxypropylmethylcellulose (Type 2910, viscosity: 3 centistokes) | 378 g |
| Titanium oxide (TiO$_2$) | 162 g |
| Sterilized Talc (trade name) [produced by Matsumura Sangyo Co. Ltd. (Japan)] | 162 g |
| Low-substituted hydroxypropyl cellulose LH-32 (hydroxypropoxyl group contents: 8.8 weight %) | 270 g |
| Mannitol | 378 g |
| Purified water | 5400 g |

(3) Production of Enteric Coated Granules having a Core

A centrifugal fluidized coating granulator [manufactured by Powrex Corp. (Japan), MP-10 (Type 2)] was charged with 1560 g of the above film-undercoated granules having a core. With the inlet air temperature and the temperature of the loading being controlled at 70° C. and about 40° C., respectively, an enteric film coating liquid (A) of the following composition prepared in advance was sprayed in accordance with the tangential spray method at a spray rate of 19 g/min. The specified amount 6048 g of the enteric film coating liquid had been sprayed.

Enteric Film Coating Liquid (A):

| | |
|---|---|
| Eudragit L30D-55 | 4032 g |
| Eudragit NE30D | 447.8 g |
| Triethyl citrate | 269.3 g |
| Glyceryl monostearate | 86.4 g |
| Polysorbate 80 | 25.9 g |
| Ferric oxide | 0.86 g |
| Ferric oxide (yellow) | 0.86 g |
| Citric acid anhydrous | 0.72 g |
| Purified water | 2624 g |

Following this, with the inlet air temperature and the temperature of the loading being controlled at 72° C. and about 42° C., respectively, an enteric film coating liquid (B) of the following composition prepared in advance was sprayed in accordance with the tangential spray method at a spray rate of 19 g/min. The specified amount 819 g of the enteric film coating liquid had been sprayed.

Enteric Film Coating Liquid (B):

| | |
|---|---|
| Eudragit L30D-55 | 609.6 g |
| Eudragit NE30D | 68.0 g |
| Polyethylene glycol 6000 | 20.4 g |
| Glyceryl monostearate | 12.0 g |
| Polysorbate 80 | 3.6 g |
| Ferric oxide | 0.12 g |
| Ferric oxide (yellow) | 0.12 g |
| Citric acid anhydrous | 0.24 g |
| Purified water | 846.7 g |

(4) Production of Enteric Coated and Mannitol Coated Granules having a Core

Following (3), while the inlet air temperature and the temperature of the loading being controlled at 65° C. and about 38° C., respectively, an film coating liquid of the following composition prepared in advance was sprayed in accordance with the tangential spray method at a spray rate of 19 g/min. using a centrifugal fluidized coating granulator [manufactured by Powrex Corp. (Japan), MP-10 (Type 2)]. The spraying operation was stopped when the specified amount 882 g of the film coating liquid had been sprayed, and then drying was carried out in the granulator for 17 minutes. The resulting granules were sieved through a #35 circular sieve (420 pun) and a #60 circular sieve (250 μm) to provide 2825 g of enteric coated and mannitol coated granules having a core.

The average particle diameter of the obtained granules was 330.5 μm.

Film Coating Liquid:

| | |
|---|---|
| Mannitol | 180 g |
| Purified water | 1080 g |

(5) Production of Mixed Powders

To 270 g of the above enteric coated and mannitol coated granules having a core were added 204.0 g of mannitol, 30 g of low-substituted hydroxypropyl cellulose LH-33 (hydroxypropoxyl group contents: 5.8 weight %), 30 g of crystalline cellulose [CEOLUS KG-801 (trade name), manufactured by Asahi Chemical Co., Ltd. (Japan)], 15 g of crospovidone, 3 g of citric acid anhydrous, 9 g of aspartame, 6 g of magnesium stearate and 3 g of flavor [STRAWBERRY DURAROME (trade name), manufactured by Nihon Filmenich Co., Ltd. (Japan)], which was admixed in a bag to give mixed powders.

(6) Production of Orally Disintegrable Tablets 570 g of the above mixed powders were tabletted using Autograph (trade name; compressing force measurement apparatus) with a punch having a beveled edge, 13 mm in diameter, at a tabletting pressure of 1.5 ton/cm$^2$, to provide tablets each weighing 570 mg.

The hardness and oral disintegration time of each tablet thus obtained were 3.1 kg and 22 seconds, respectively.

The acid-resistance of the obtained tablet was 2.5%.

Example 7

(1) Production of Granules having a Core

A centrifugal fluidized coating granulator [manufactured by Powrex Corp. (Japan), MP-10 (Type 2)] was charged with 750 g of Nonpareil 105 (trade name) (particle diameter of 100 to 200 μm). With the inlet air temperature and the temperature of the loading being controlled at 75° C. and about 30° C. respectively, the Nonpareil was coated by spraying a bulk liquid of the following composition prepared in advance in accordance with the tangential spray method at a spray rate of 20 g/min. The spraying operation was stopped when the specified amount 4717.5 g of the bulk liquid had been sprayed, and then drying was carried out in the granulator for 10 minutes to provide 1842 g of granules having a core.

Bulk Liquid:

| | |
|---|---:|
| Lansoprazole | 900 g |
| Magnesium carbonate | 300 g |
| Low-substituted hydroxypropyl cellulose LH-32 (hydroxypropoxyl group contents: 8.8 weight %) | 150 g |
| Hydroxypropyl cellulose (Type SSL) | 300 g |
| Purified water | 3900 g |

(2) Production of Film-Undercoated Granules having a Core

A centrifugal fluidized coating granulator [manufactured by Powrex Corp. (Japan), MP-10 (Type 2)] was charged with 1842 g of the above granules having a core. With the inlet air temperature and the temperature of the loading being controlled at 74° C. and about 38° C., respectively, an undercoating liquid of the following composition prepared in advance was sprayed in accordance with the tangential spray method at a spray rate of 19 g/min. The spraying operation was stopped when the specified amount 5365 g of the undercoating liquid had been sprayed, and then drying was carried out in the granulator for 9 minutes. The resulting granules were sieved through a #42 circular sieve (350 μm) and a #100 circular sieve (150 μm) to provide 2770 g of film-undercoated granules having a core.

Undercoating Liquid:

| | |
|---|---:|
| Hydroxypropylmethylcellulose (Type 2910, viscosity: 3 centistokes) | 378 g |
| Titanium oxide (TiO$_2$) | 162 g |
| Sterilized Talc (trade name) [produced by Matsumura Sangyo Co. Ltd. (Japan)] | 162 g |
| Low-substituted hydroxypropyl cellulose LH-32 (hydroxypropoxyl group contents: 8.8 weight % ) | 270 g |
| Mannitol | 378 g |
| Purified water | 5400 g |

(3) Production of Enteric Coated Granules having a Core

A centrifugal fluidized coating granulator [manufactured by Powrex Corp. (Japan), MP-10 (Type 2)] was charged with 1300 g of the above film-undercoated granules having a core. With the inlet air temperature and the temperature of the loading being controlled at 78° C. and about 39° C., respectively, an enteric film coating liquid (A) of the following composition prepared in advance was sprayed in accordance with the tangential spray method at a spray rate of 21 g/min. The spraying operation was stopped when the specified amount 5040 g of the enteric film coating liquid had been sprayed, and then drying was carried out in the granulator for 16 minutes. The resulting granules were sieved through a #35 circular sieve (420 μm) and a #60 circular sieve (250 μm) to provide 2453 g of enteric coated granules having a core.

Enteric Film Coating Liquid (A):

| | |
|---|---:|
| Eudragit L30D-55 | 4032 g |
| Eudragit NE30D | 447.8 g |
| Triethyl citrate | 269.3 g |
| Glyceryl monostearate | 86.4 g |
| Polysorbate 80 | 25.9 g |
| Ferric oxide | 0.86 g |
| Ferric oxide (yellow) | 0.86 g |
| Citric acid anhydrous | 0.72 g |
| Purified water | 2624 g |

A centrifugal fluidized coating granulator [manufactured by Powrex Corp. (Japan), MP-10 (Type 2)] was charged with 1000 g of the above enteric coated granules having a core. With the inlet air temperature and the temperature of the loading being controlled at 80° C. and about 38° C., respectively, an enteric film coating liquid (B) of the following composition prepared in advance was sprayed in accordance with the tangential spray method at a spray rate of 19 g/min. The specified amount 273 g of the enteric film coating liquid had been sprayed.

Enteric Film Coating Liquid (B):

| | |
|---|---:|
| Eudragit L30D-55 | 610.4 g |
| Eudragit NE30D | 68.0 g |
| Polyethylene glycol 6000 | 20.4 g |
| Glyceryl monostearate | 12.0 g |
| Polysorbate 80 | 3.6 g |
| Ferric oxide | 0.12 g |
| Ferric oxide (yellow) | 0.12 g |
| Citric acid anhydrous | 0.24 g |
| Purified water | 845.12 g |

(4) Production of Enteric Coated and Mannitol Coated Granules having a Core

Following (3), while the inlet air temperature and the temperature of the loading being controlled at 75° C. and about 35° C., respectively, an film coating liquid of the following composition prepared in advance was sprayed in accordance with the tangential spray method at a spray rate of 20 g/min. using a centrifugal fluidized coating granulator [manufactured by Powrex Corp. (Japan), MP-10 (Type 2)]. The spraying operation was stopped when the specified amount 294 g of the film coating liquid had been sprayed, and then drying was carried out in the granulator for 10 minutes. The resulting granules were sieved through a #35 circular sieve (420 μm) and a #60 circular sieve (250 μm) to provide 1061 g of enteric coated and mannitol coated granules having a core.

The average particle diameter of the obtained granules was 307.1 μm.

Film Coating Liquid:

| | |
|---|---:|
| Mannitol | 120 g |
| Purified water | 720 g |

(5) Production of Mixed Powders

To 270 g of the above enteric coated and mannitol coated granules having a core were added 207 g of mannitol, 30 g of low-substituted hydroxypropyl cellulose LH-33 (hydroxypropoxyl group contents: 5.8 weight %), 30 g of crystalline cellulose [CEOLUS KG-801 (trade name), manufactured by Asahi Chemical Co., Ltd. (Japan)], 15 g of crospovidone, 3 g of citric acid anhydrous, 9 g of aspartame, 6 g of magnesium stearate and 3 g of flavor [STRAWBERRY DURAROME (trade name), manufactured by Nihon Filmenich Co., Ltd. (Japan)], which was admixed in a bag to give mixed powders.

(6) Production of Orally Disintegrable Tablets 570 g of the above mixed powders were tabletted using Autograph (trade name; compressing force measurement apparatus) with a punch having a beveled edge, 13 mm in diameter, at a tabletting pressure of 1.5 ton/cm$^2$, to provide tablets each weighing 570 mg.

The hardness and oral disintegration time of each tablet thus obtained were 3.2 kg and 24 seconds, respectively.

Example 8

(1) Production of Granules Having a Core

A centrifugal fluidized coating granulator [manufactured by Powrex Corp. (Japan), MP-10 (Type 2)] was charged with 900 g of Nonpareil 105T (trade name) (particle diameter of 100 to 200 μm). With the inlet air temperature and the temperature of the loading being controlled at 71 to 78° C. and about 31° C. respectively, the Nonpareil was coated by spraying a bulk liquid of the following composition prepared in advance in accordance with the tangential spray method at a spray rate of 21 g/min. The spraying operation was stopped when the specified amount 5550 g of the bulk liquid had been sprayed, and then drying was carried out in the granulator for 21 minutes. The resulting granules were sieved through a #42 circular sieve (350 μm) and a #100 circular sieve (150 μm) to provide 1723 g of granules having a core.

Bulk Liquid:

| | |
|---|---|
| Lansoprazole | 1080 g |
| Magnesium carbonate | 360 g |
| Low-substituted hydroxypropyl cellulose LH-32 (hydroxypropoxyl group contents: 8.8 weight %) | 180 g |
| Hydroxypropyl cellulose (Type SSL) | 360 g |
| Purified water | 4680 g |

(2) Production of Film-Undercoated Granules having a Core

A centrifugal fluidized coating granulator [manufactured by Powrex Corp. (Japan), MP-10 (Type 2)] was charged with 2074 g of the above granules having a core. With the inlet air temperature and the temperature of the loading being controlled at 77° C. and about 41° C., respectively, an undercoating liquid of the following composition prepared in advance was sprayed in accordance with the tangential spray method at a spray rate of 21 g/min. The spraying operation was stopped when the specified amount 2787 g of the undercoating liquid had been sprayed, and then drying was carried out in the granulator for 13 minutes. The resulting granules were sieved through a #42 circular sieve (350 μm) and a #100 circular sieve (150 μm) to provide 1958 g of film-undercoated granules having a core.

Undercoating Liquid:

| | |
|---|---|
| Hydroxypropylmethylcellulose (Type 2910, viscosity: 3 centistokes) | 252 g |
| Titanium oxide (TiO$_2$) | 108 g |
| Sterilized Talc (trade name) [produced by Matsumura Sangyo Co. Ltd. (Japan)] | 108 g |
| Low-substituted hydroxypropyl cellulose LH-32 (hydroxypropoxyl group contents: 8.8 weight %) | 180 g |
| Mannitol | 252 g |
| Purified water | 3600 g |

(3) Production of Enteric Coated Granules having a Core

A centrifugal fluidized coating granulator [manufactured by Powrex Corp. (Japan), MP-10 (Type 2)] was charged with 1100 g of the above film-undercoated granules having a core. With the inlet air temperature and the temperature of the loading being controlled at 80° C. and about 41° C., respectively, an enteric film coating liquid (A) of the following composition prepared in advance was sprayed in accordance with the tangential spray method at a spray rate of 22 g/min. The specified amount 1365 g of the enteric film coating liquid had been sprayed.

Enteric Film Coating Liquid (A):

| | |
|---|---|
| Eudragit L30D-55 | 1017.3 g |
| Eudragit NE30D | 113.3 g |
| Polyethylene glycol 6000 | 34.0 g |
| Glyceryl monostearate | 20.0 g |
| Polysorbate 80 | 6.0 g |
| Ferric oxide | 0.2 g |
| Ferric oxide (yellow) | 0.2 g |
| Citric acid anhydrous | 0.4 g |
| Purified water | 1410.8 g |

Following this, with the inlet air temperature and the temperature of the loading being controlled at 76° C. and about 41° C., respectively, an enteric film coating liquid (B) of the following composition prepared in advance was sprayed in accordance with the tangential spray method at a spray rate of 22 g/min. The specified amount 5040 g of the enteric film coating liquid had been sprayed.

Enteric Film Coating Liquid (B):

| | |
|---|---|
| Eudragit L30D-55 | 3360 g |
| Eudragit NE30D | 373.2 g |
| Triethyl citrate | 224.4 g |
| Glyceryl monostearate | 72.0 g |
| Polysorbate 80 | 21.6 g |
| Ferric oxide | 0.72 g |
| Ferric oxide (yellow) | 0.72 g |
| Citric acid anhydrous | 0.6 g |
| Purified water | 1706.8 g |

Following this, with the inlet air temperature and the temperature of the loading being controlled at 80° C. and about 42° C., respectively, an enteric film coating liquid (A) of the above mentioned composition prepared in advance was sprayed in accordance with the tangential spray method at a spray rate of 21 g/min. The specified amount 682.5 g of the enteric film coating liquid had been sprayed.

(4) Production of Enteric Coated and Mannitol Coated Granules having a Core Following (3), with the inlet air temperature and the temperature of the loading being controlled at 80° C. and about 36° C., respectively, an film coating liquid of the following composition prepared in advance was sprayed in accordance with the tangential spray method at a spray rate of 22 g/min. using a centrifugal fluidized coating granulator [manufactured by Powrex Corp. (Japan), MP-10 (Type 2)].

The spraying operation was stopped when the specified amount 735 g of the film coating liquid had been sprayed, and then drying was carried out in the granulator for 10 minutes. The resulting granules were sieved through a #35 circular sieve (420 μm) and a #60 circular sieve (250 μm) to provide 2319.5 g of enteric coated and mannitol coated granules having a core.

The average particle diameter of the obtained granules was 392.7 μm.

Film Coating Liquid:

| | |
|---|---|
| Mannitol | 100 g |
| Purified water | 600 g |

(5) Production of Mixed Powders

To 270 g of the above enteric coated and mannitol coated granules having a core were added 204.0 g of mannitol, 30 g of low-substituted hydroxypropyl cellulose LH-33 (hydroxypropoxyl group contents: 5.8 weight %), 30 g of crystalline cellulose [CEOLUS KG-801 (trade name), manufactured by Asahi Chemical Co., Ltd. (Japan)], 15 g of crospovidone, 3 g of citric acid anhydrous, 9 g of aspartame, 6 g of magnesium stearate and 3 g of flavor [STRAWBERRY DURAROME (trade name), manufactured by Nihon Filmenich Co., Ltd. (Japan)], which was admixed in a bag to give mixed powders.

(6) Production of Orally Disintegrable Tablets 570 g of the above mixed powders were tabletted using Autograph (trade name; compressing force measurement apparatus) with a punch having a beveled edge, 12 mm in diameter, at a tabletting pressure of 1.5 ton/cm$^2$, to provide tablets each weighing 570 mg.

The hardness and oral disintegration time of each tablet thus obtained were 3.7 kg and 35 seconds, respectively.

The acid-resistance of the obtained tablet was 3.4%.

Example 9

(1) Production of Granules having a Core

A centrifugal fluidized coating granulator [manufactured by Powrex Corp. (Japan), MP-10 (Type 2)] was charged with 300 g of Nonpareil 105 (70-140) (particle diameter of 100 to 200 μm). With the inlet air temperature and the temperature of the loading being controlled at 85° C. and about 28° C. respectively, the Nonpareil was coated by spraying a bulk liquid of the following composition prepared in advance in accordance with the tangential spray method at a spray rate of 20 g/min. The spraying operation was stopped when the specified amount of the bulk liquid had been sprayed, and then drying was carried out in the granulator for 7 minutes. The resulting granules were sieved through a #48 circular sieve (300 μm) and a #100 circular sieve (150 μm) to provide 757 g of granules having a core.

Bulk Liquid:

| | |
|---|---|
| Lansoprazole | 300 g |
| Magnesium carbonate | 100 g |
| L-HPC | 50 g |
| HPC (Type SSL) | 100 g |
| Water | 1650 g |

(2) Production of Film-Undercoated Granules having a Core

A centrifugal fluidized coating granulator [manufactured by Powrex Corp. (Japan), MP-10 (Type 2)] was charged with 680 g of the above granules having a core. With the inlet air temperature and the temperature of the loading being controlled at 70° C. and about 36° C., respectively, an undercoating liquid of the following composition prepared in advance was sprayed in accordance with the tangential spray method at a spray rate of 10 g/min. to provide 672 g of film-undercoated granules having a core.

Undercoating Liquid:

| | |
|---|---|
| HPMC (Type 2910, viscosity: 3 centistokes) | 32 g |
| Talc | 8 g |
| Water | 760 g |

(3) Production of Enteric Coated Granules having a Core

A centrifugal fluidized coating granulator [manufactured by Powrex Corp. (Japan), MP-10 (Type 2)] was charged with 450 g of the above film-undercoated granules having a core. With the inlet air temperature and the temperature of the loading being controlled at 65° C. and about 36° C., respectively, an enteric film coating liquid of the following composition prepared in advance was sprayed in accordance with the tangential spray method at a spray rate of 17 g/min. The coated powders were dried in vacuum at 40° C. for 16 hours, and sieved through a #42 circular sieve (355 μm) and a #80 circular sieve (177 μm) to provide 950 g of enteric coated granules having a core.

The average particle diameter of the obtained granules was 285.4 μm.

Enteric Film Coating Liquid:

| | |
|---|---|
| Eudragit L30D-55 | 1078.3 g |
| Eudragit NE30D | 138.5 g |
| Triethyl citrate | 46.0 g |
| Glyceryl monostearate | 16.5 g |
| Talc | 16.0 g |
| Polysorbate 80 | 9.0 g |
| Iron oxide | 0.5 g |
| Water | 2038.5 g |

| Sieve | weight ratio |
|---|---|
| #18 (850 μm) on | 0% |
| #30 (500 μm) on | 0% |
| #200 (75 μm) on | 100% |
| #200 (75 μm) pass | 0% |

(4) Production of Granulated Powders

A fluidized bed granulator [manufactured by Powrex Corp. (Japan), LAB-1] was charged with 1321.2 g of erythritol [manufactured by Nikken Chemical Co., Ltd. (Japan)], 360.0 g of low-substituted hydroxypropyl cellulose LH-32 [hydroxypropoxyl group contents of 8.8%, manufactured by Shin-Etsu Chemical Co., Ltd. (Japan)], 18.0 g of citric acid anhydrous, and 1.8 g of aspartame, and granulation was carried out while spraying a solution which was prepared by dissolving 3.6 g of polyethylene glycol (PEG-6000) in 896.4 ml of purified water. The granules were dried to provide granulated powders. To the granulated powders were added 90.0 g of crospovidone and 5.4 g of magnesium stearate, which was admixed in a bag to give mixed powders.

(5) Production of Orally Disintegrable Tablets 200.0 g of the above enteric coated granules having a core and 300.0 g of the above mixed powders were tabletted using Autograph (trade name; compressing force measurement apparatus) with a punch having a beveled edge, 11 mm in diameter, at a tabletting pressure of 1.0 ton/cm$^2$, to provide tablets each weighing 500 mg.

The hardness, the oral disintegration time and remaining ratio after acid-resistance test of each tablet thus obtained were 4.2 kg, 27 seconds and 96.3%, respectively.

INDUSTRIAL APPLICABILITY

The orally disintegrable tablet of the present invention has superior disintegrability or dissolution so that it can be used for treatment or prevention of various diseases, as an orally disintegrable tablet capable of being administered to the aged or children and easily administered without water. Also, because the orally disintegrable tablet of the present invention contains fine granules having the average particle diameter and an enteric coating layer such that it will not impart roughness in mouth, it can be administered easily without discomfort at the administration and has superior acid-resistance.

Further, because the orally disintegrable tablet of the present invention has a suitable strength such that it will not be substantially damaged through production processes or circulation processes, it is superior in stability for long-term storage and easy of use at the administration.

Further, because the fine granule of the present invention is characterized in that it stably retains the acid-labile physiologically active substance, contains the physiologically active substance in high content, be small and has superior stability, it can by used for producing various compact pharmaceutical preparations such as tablets, capsules, suspensions and so forth. Such preparations are easy of use at the administration. In addition, the fine granule of the present invention has superior acid-resistance after compression.

The invention claimed is:

1. An orally disintegrable tablet, which comprises: (i) fine granules comprising a composition coated with an enteric coating layer, said composition comprising: 10 weight % or more of lansoprazole or a salt thereof relative to the composition; and a basic inorganic salt selected from the group consisting of a salt of magnesium and a salt of calcium; and (ii) an additive comprising crospovidone and a water-soluble sugar alcohol,
wherein the water-soluble sugar alcohol is comprised in the tablet separately from the fine granules,
the enteric coating layer is about 30-70 weight % relative to the fine granule,
the enteric coating layer comprises a methacrylic acid copolymer as an aqueous enteric polymer agent,
the orally disintegrable tablet is administerable without water, an oral disintegration time of the orally disintegrable tablet is one minute or less,
the orally disintegrable tablet is not an effervescent, and the composition does not comprise alkaline metal carbonate.

2. The orally disintegrable tablet of claim 1, wherein the composition coated by an enteric coating layer is further coated by a coating layer which comprises a water-soluble sugar alcohol.

3. The orally disintegrable tablet of claim 1, wherein the additive further comprises at least one material selected from the group consisting of (i) crystalline cellulose and (ii) low-substituted hydroxypropyl cellulose.

4. The orally disintegrable tablet of claim 1, wherein a particle diameter of the fine granules is practically 425 μm or less.

5. The orally disintegrable tablet of claim 1, wherein a particle diameter of the fine granules is practically 400 μm or less.

6. The orally disintegrable tablet of claim 1, wherein the composition comprises a core being coated with the lansoprazole or the salt thereof and the basic inorganic salt, said core comprising crystalline cellulose and lactose.

7. The orally disintegrable tablet of claim 6, wherein the core comprises lactose in an amount of 50 weight % or more.

8. The orally disintegrable tablet of claim 6, wherein the core comprises crystalline cellulose in an amount from 40 to 50 weight % and the lactose in an amount from 50 to 60 weight %.

9. The orally disintegrable tablet of claim 1, wherein the composition comprises the lansoprazole or the salt thereof in an amount of 20 weight % or more.

10. The orally disintegrable tablet of claim 1, wherein the composition comprises the lansoprazole or the salt thereof in an amount from 20 to 50 weight %.

11. The orally disintegrable tablet of claim 1, wherein the fine granules are produced by fluidized-bed granulation method.

12. The orally disintegrable tablet of claim 1, wherein the enteric coating layer further comprises a sustained-release agent.

13. The orally disintegrable tablet of claim 12, wherein the sustained-release agent is a methacrylate copolymer.

14. The orally disintegrable tablet of claim 12, wherein the sustained-release agent is contained in an amount from 5 to 15 weight % relative to 100 weight % of the aqueous enteric polymer agent.

15. The orally disintegrable tablet of claim 1, wherein the water-soluble sugar alcohol is erythritol.

16. The orally disintegrable tablet of claim 1, wherein the water-soluble sugar alcohol is mannitol.

17. The orally disintegrable tablet of claim 12, wherein the water-soluble sugar alcohol is contained in an amount from 5 to 97 weight % relative to 100 weight % of the orally disintegrable tablet apart from the fine granules.

18. The orally disintegrable tablet of claim 3, wherein the crystalline cellulose is contained in an amount from 3 to 50 weight % relative to 100 weight % of the tablet apart from the fine granule.

19. The orally disintegrable tablet of claim 1, wherein the tablet comprises no lubricant inside the tablet.

20. The orally disintegrable tablet of claim 1, wherein the enteric coating layer has a thickness from 20 to 70 μm.

21. The orally disintegrable tablet of claim 1, wherein the oral disintegration time of the tablet is about 40 seconds or less.

22. The orally disintegrable tablet of claim 1, wherein the orally disintegrable tablet has a tablet hardness in a range from about 1 kg to about 20 kg.

* * * * *

UNITED STATES PATENT AND TRADEMARK OFFICE
CERTIFICATE OF CORRECTION

PATENT NO. : 9,901,546 B2  
APPLICATION NO. : 14/287740  
DATED : February 27, 2018  
INVENTOR(S) : Shimizu et al.

Page 1 of 2

It is certified that error appears in the above-identified patent and that said Letters Patent is hereby corrected as shown below:

On the Title Page

Column 2, item (56), under "Other Publications", Line 9, delete "Bahavior" and insert -- Behavior --.

In the Specification

Column 4, Line 32, after "97 weight" insert -- % --.

Column 5, Line 63, after "400" insert -- µm. --.

Column 7, Line 8, after "hydroxy" delete ",".

Column 7, Line 59, delete "[2,5MgO" and insert -- [2.5MgO --.

Column 8, Line 54, after "weight" delete "4" and insert -- % --.

Column 9, Line 14, delete "KOLLICOAT MAE® 30DP" and insert -- KOLLICOAT® MAE30DP --.

Column 9, Line 23, delete "methylacrylic" and insert -- methacrylic --.

Column 9, Line 25, delete "methylacrylic" and insert -- methacrylic --.

Column 12, Line 25, delete "disintegrants)" and insert -- disintegrant(s) --.

Column 14, Line 65, delete "250 µl" and insert -- 250 µm --.

Column 26, Line 21, delete "(355 pin)" and insert -- (355 µm) --.

Column 26, Line 25, delete "pun." and insert -- µm. --.

Signed and Sealed this  
Tenth Day of July, 2018

Andrei Iancu  
*Director of the United States Patent and Trademark Office*

CERTIFICATE OF CORRECTION (continued)
U.S. Pat. No. 9,901,546 B2

Column 29, Line 17, delete "350 µl" and insert -- 350 µm --.

Column 30, Line 45, delete "pun)" and insert -- µm) --.

Column 37, Line 30, delete "can by" and insert -- can be --.

In the Claims

Column 38, in Claim 17, Line 42, delete "claim 12," and insert -- claim 2, --.